(12) United States Patent
Hu et al.

(10) Patent No.: US 9,353,188 B2
(45) Date of Patent: May 31, 2016

(54) MODULATORS OF PLEXIN B2 ACTIVITY

(75) Inventors: Guofu Hu, Wellesley, MA (US); Wenhao Yu, Newton, MA (US)

(73) Assignees: President and Fellows of Harvard College, Cambridge, MA (US); Tufts Medical Center, Inc., Boston, MA (US)

( * ) Notice: Subject to any disclaimer, the term of this patent is extended or adjusted under 35 U.S.C. 154(b) by 113 days.

(21) Appl. No.: 14/008,085

(22) PCT Filed: Mar. 28, 2012

(86) PCT No.: PCT/US2012/030923
§ 371 (c)(1),
(2), (4) Date: Dec. 26, 2013

(87) PCT Pub. No.: WO2012/135332
PCT Pub. Date: Oct. 4, 2012

(65) Prior Publication Data
US 2014/0105903 A1    Apr. 17, 2014

Related U.S. Application Data

(60) Provisional application No. 61/468,271, filed on Mar. 28, 2011, provisional application No. 61/543,992, filed on Oct. 6, 2011.

(51) Int. Cl.
*A61K 39/00* (2006.01)
*C07K 16/40* (2006.01)
*C07K 16/30* (2006.01)
*C07K 14/715* (2006.01)
*G01N 33/68* (2006.01)
*C07K 16/28* (2006.01)
*C07K 14/71* (2006.01)
*C12N 15/113* (2010.01)

(52) U.S. Cl.
CPC .............. *C07K 16/40* (2013.01); *C07K 14/71* (2013.01); *C07K 14/715* (2013.01); *C07K 16/28* (2013.01); *C07K 16/30* (2013.01); *G01N 33/6863* (2013.01); *A61K 2039/505* (2013.01); *C07K 2317/34* (2013.01); *C07K 2317/73* (2013.01); *C07K 2317/76* (2013.01); *C12N 15/1138* (2013.01); *C12N 2310/14* (2013.01)

(58) Field of Classification Search
None
See application file for complete search history.

(56) References Cited

U.S. PATENT DOCUMENTS

| 2008/0207497 A1 | 8/2008 | Ramakrishna et al. |
| 2008/0292546 A1 | 11/2008 | Clarke et al. |
| 2010/0008935 A1* | 1/2010 | Borlak et al. ............... 424/172.1 |
| 2010/0120781 A1 | 5/2010 | Neamati |
| 2010/0239581 A1 | 9/2010 | Joseloff et al. |

FOREIGN PATENT DOCUMENTS

WO    WO-2008/055889 A1    5/2008

OTHER PUBLICATIONS

International Search Report from related application PCT/US12/30923, mailed Aug. 31, 2012.
Written Opinion of the International Searching Authority from related application PCT/US12/30923, mailed Aug. 31, 2012.

* cited by examiner

*Primary Examiner* — Maher Haddad
(74) *Attorney, Agent, or Firm* — Foley Hoag LLP

(57) ABSTRACT

Disclosed herein are novel compositions and methods for the inhibition of Plexin B2-mediated Angiogenin activity. Such compositions and methods are useful, for example, for the treatment of cancer, the treatment of wet AMD and the inhibition of angiogenesis. Also disclosed herein are methods of determining whether a test agent is a modulator of Plexin B2 activity.

2 Claims, 16 Drawing Sheets

Figure 1

ANG Binding Epitopes of Plexin B2:

Epitope 1 (SEQ ID NO: 1): GTSSEYDSILVEINKRVK

Epitope 2 (SEQ ID NO: 2): LDKVHAKMEANRNAC

Epitope 3 (SEQ ID NO: 3): RDGLRGTAVLQRGGLNL

Figure 2

Complete Human Plexin B2 amino acid sequence (SEQID NO: 4):

```
1     MALQLWALTL LGLLGAGASL RPRKLDFFRS EKELNHLAVD EASGVVYLGA VNALYQLDAK
61    LQLEQQVATG PALDNKKCTP PIEASQCHEA EMTDNVNQLL LLDPPRKRLV ECGSLFKGIC
121   ALRALSNISL RLFYEDGSGE KSFVASNDEG VATVGLVSST GPGGDRVLFV GKGNGPHDNG
181   IIVSTRLLDR TDSREAFEAY TDHATYKAGY LSTNTQQFVA AFEDGPYVFF VFNQQDKHPA
241   RNRTLLARMC REDPNYYSYL EMDLQCRDPD IHAAAFGTCL AASVAAPGSG RVLYAVFSRD
301   SRSSGGPGAG LCLFPLDKVH AKMEANRNAC YTGTREARDI FYKPFHGDIQ CGGHAPGSSK
361   SFPCGSEHLP YPLGSRDGLR GTAVLQRGGL NLTAVTVAAE NNHTVAFLGT SDGRILKVYL
421   TPDGTSSEYD SILVEINKRV KRDLVLSGDL GSLYAMTQDK VFRLPVQECL SYPTCTQCRD
481   SQDPYCGWCV VEGRCTRKAE CPRAEEASHW LWSRSKSCVA VTSAQPQNMS RRAQGEVQLT
541   VSPLPALSEE DELLCLFGES PPHPARVEGE AVICNSPSSI PVTPPGQDHV AVTIQLLLRR
601   GNIFLTSYQY PFYDCRQAMS LEENLPCISC VSNRWTCQWD LRYHECREAS PNPEDGIVRA
661   HMEDSCPQFL GPSPLVIPMN HETDVNFQGK NLDTVKGSSL HVGSDLLKFM EPVTMQESGT
721   FAFRTPKLSH DANETLPLHL YVKSYGKNID SKLHVTLYNC SFGRSDCSLC RAANPDYRCA
781   WCGGQSRCVY EALCNTTSEC PPPVITRIQP ETGPLGGGIR ITILGSNLGV QAGDIQRISV
841   AGRNCSFQPE RYSVSTRIVC VIEAAETPFT GGVEVDVFGK LGRSPPNVQF TFQQPKPLSV
901   EPQQGPQAGG TTLTIHGTHL DTGSQEDVRV TLNGVPCKVT KFGAQLQCVT GPQATRGQML
961   LEVSYGGSPV PNPGIFFTYR ENPVLRAFEP LRSFASGGRS INVTGQGFSL IQRFAMVVIA
1021  EPLQSWQPPR EAESLQPMTV VGTDYVFHND TKVVFLSPAV PEEPEAYNLT VLIEMDGHRA
1081  LLRTEAGAFE YVPDPTFENF TGGVKKQVNK LIHARGTNLN KAMTLQEAEA FVGAERCTMK
1141  TLTETDLYCE PPEVQPPPKR RQKRDTTHNL PEFIVKFGSR EWVLGRVEYD TRVSDVPLSL
1201  ILPLVIVPMV VVIAVSVYCY WRKSQQAERE YEKIKSQLEG LEESVRDRCK KEFTDLMIEM
1261  EDQTNDVHEA GIPVLDYKTY TDRVFFLPSK DGDKDVMITG KLDIPEPRRP VVEQALYQFS
1321  NLLNSKSFLI NFIHTLENQR EFSARAKVYF ASLLTVALHG KLEYYTDIMH TLFLELLEQY
1381  VVAKNPKLML RRSETVVERM LSNWMSICLY QYLKDSAGEP LYKLFKAIKH QVEKGPVDAV
1441  QKKAKYTLND TGLLGDDVEY APLTVSVIVQ DEGVDAIPVK VLNCDTISQV KEKIIDQVYR
1501  GQPCSCWPRP DSVVLEWRPG STAQILSDLD LTSQREGRWK RVNTLMHYNV RDGATLILSK
1561  VGVSQQPEDS QQDLPGERHA LLEEENRVWH LVRPTDEVDE GKSKRGSVKE KERTKAITEI
1621  YLTRLLSVKG TLQQFVDNFF QSVLAPGHAV PPAVKYFFDF LDEQAEKHNI QDEDTIHIWK
1681  TNSLPLRFWV NILKNPHFIF DVHVHEVVDA SLSVIAQTFM DACTRTEHKL SRDSPSNKLL
1741  YAKEISTYKK MVEDYYKGIR QMVQVSDQDM NTHLAEISRA HTDSLNTLVA LHQLYQYTQK
1801  YYDEIINALE EDPAAQKMQL AFRLQQIAAA LENKVTDL
```

Figure 3

Complete Human Angiogenin amino acid sequence (SEQID NO: 5):

```
1    MVMGLGVLLL VFVLGLGLTP PTLAQDNSRY THFLTQHYDA KPQGRDDRYC ESIMRRRGLT
61   SPCKDINTFI HGNKRSIKAI CENKNGNPHR ENLRISKSSF QVTTCKLHGG SPWPPCQYRA
121  TAGFRNVVVA CENGLPVHLD QSIFRRP
```

Figure 6
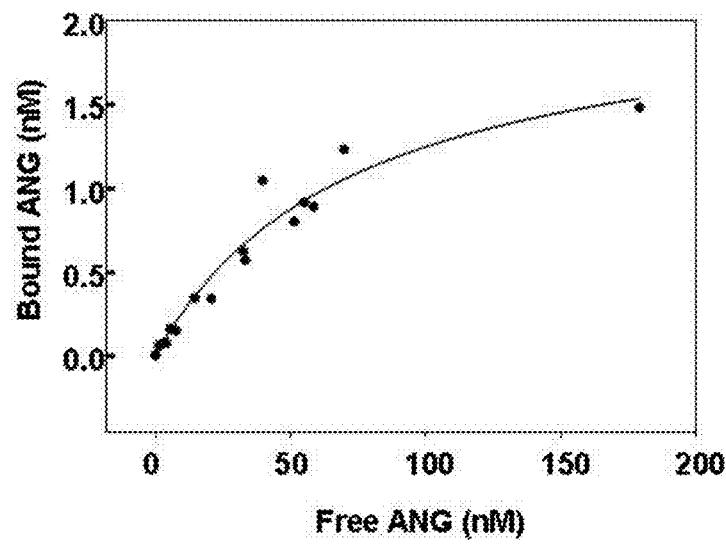
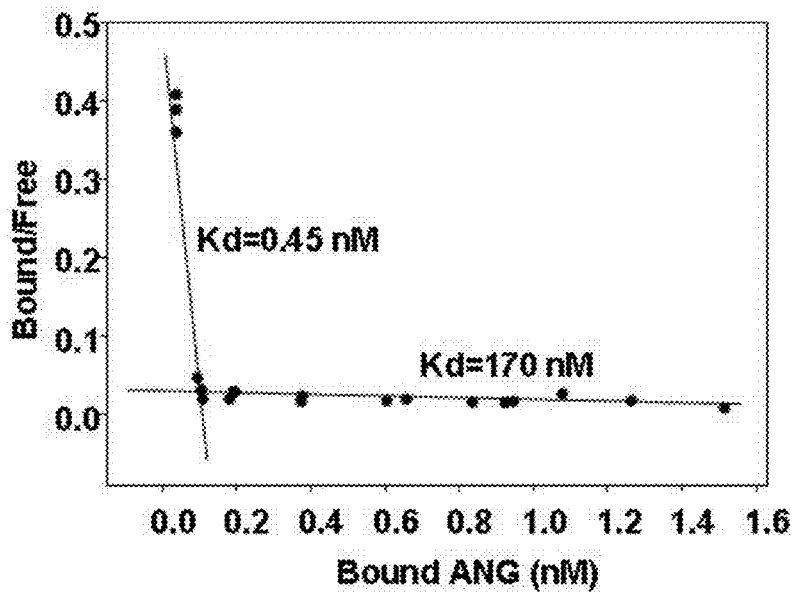

under 35 U.S.C.
MODULATORS OF PLEXIN B2 ACTIVITY

RELATED APPLICATIONS

This application is a national stage filing under 35 U.S.C. 371 of PCT/US12/030923, filed Mar. 28, 2012, which claims the benefit of priority to U.S. Provisional Patent Application Ser. No. 61/468,271, filed Mar. 28, 2011 and U.S. Provisional Patent Application Ser. No. 61/543,992, filed Oct. 6, 2011; each of which is hereby incorporated by reference in its entirety.

GOVERNMENT INTEREST

This invention was made with Government support under National Institutes of Health Grant CA105241. The Government has certain rights in the invention.

BACKGROUND

The small, secreted protein Angiogenin ("ANG") is a potent inducer of angiogenesis that has been implicated in the establishment, growth and metastasis of various tumors. Inhibition of ANG activity is therefore an attractive therapeutic strategy for the treatment of cancer and other angiogenesis-related diseases, such as wet age-related macular degeneration ("AMD"). However, despite ANG's important role in both blood vessel formation and cancer, the receptors that bind to angiogenin ANG to mediate its angiogenic and tumor promoting activity remain unknown. Identification and characterization of ANG receptors would provide a novel therapeutic target for the treatment of cancer and the inhibition of ANG-mediated angiogenesis.

Thus, there is a great need for the identification and characterization of ANG receptors in order to develop novel compositions and methods for the inhibition of ANG activity, the prevention of angiogenesis and the treatment of cancer.

SUMMARY

As demonstrated herein, Plexin B2 is an ANG receptor that mediates ANG's angiogenic and tumor promoting activities. Also described herein are the Plexin B2 epitopes that contribute to ANG binding. Thus, Plexin B2 antagonists, including agents that disrupt the binding of ANG to Plexin B2 (e.g., anti-Plexin B2 antibodies), are useful, for example, for the treatment of cancer (e.g., prostate cancer or brain cancer), the inhibition of angiogenesis, and the treatment of angiogenesis-related diseases (e.g., wet AMD).

In certain embodiments, the instant invention relates to an isolated antibody or antigen binding fragment thereof that specifically binds to an epitope of Plexin B2 that contributes to ANG binding. For example, in certain embodiments the antibody or antigen binding fragment thereof binds to an epitope of Plexin B2 having an amino acid sequence of SEQ ID NO: 1, SEQ ID NO:2 or SEQ ID NO: 3. In some embodiments the antibody or antigen binding fragment thereof is monoclonal, polyclonal, chimeric, humanized or human. In certain embodiments, the antibody or antigen binding fragment thereof is a full length immunoglobulin molecule; an scFv; a Fab fragment; an Fab' fragment; an F(ab')2; an Fv; a NANOBODY®; or a disulfide linked Fv. In some embodiments the antibody or antigen binding fragment thereof binds to Plexin B2 with a dissociation constant of no greater than about $10^{-6}$ M, $10^{-7}$ M, $10^{-8}$ M or $10^{-9}$ M. In certain embodiments the antibody or antigen binding fragment thereof inhibits the binding of ANG to Plexin B2 and/or inhibits ANG-induced proliferation of a Plexin B2 expressing cell.

In certain embodiments the instant invention relates to an isolated soluble polypeptide that includes an amino acid sequence of SEQ ID NO: 1, SEQ ID NO: 2 and/or SEQ ID NO: 3, wherein the polypeptide binds to ANG. In some embodiments the polypeptide comprises no more than 25, 30, 40, 50, 60, 70, 80, 90 or 100 consecutive amino acids of SEQ ID NO: 4. In certain embodiments the polypeptide also includes an immunoglobulin constant domain (e.g., a human immunoglobulin constant domain). In some embodiments the polypeptide binds to ANG with a dissociation constant of no greater than about $10^{-6}$ M, $10^{-7}$ M, $10^{-8}$ M or $10^{-9}$ M. In certain embodiments the polypeptide inhibits ANG-induced proliferation of a Plexin B2 expressing cell.

In some embodiments, the instant invention relates to pharmaceutical composition that contains an antibody, antigen binding fragment thereof or polypeptide described herein.

In certain embodiments, the instant invention relates to a method of treating cancer (including prostate cancer or brain cancer), inhibiting angiogenesis, and/or treating wet AMD in a subject (e.g., in a subject in need thereof) that includes the step of administering to the subject a therapeutically effective amount of the antibody, antigen binding fragment thereof or polypeptide described herein In some embodiments, the instant invention relates to a method of inhibiting ANG-induced proliferation of a Plexin B2 expressing cell that includes contacting the cell with an antibody, antigen binding fragment thereof or polypeptide described herein.

In certain embodiments, the instant invention relates to a method of producing an antibody described herein that includes administering to a mammal (e.g., a mouse) a polypeptide (e.g., a soluble polypeptide) that contains an amino acid sequence of SEQ ID NO:1, SEQ ID NO: 2 and/or SEQ IN NO: 3. In some embodiments, the polypeptide contains no more than 25, 30, 40, 50, 60, 70, 80, 90 or 100 consecutive amino acids of SEQ ID NO: 4. In some embodiments the method also includes the step of isolating the antibody from the mammal. In some embodiments the mammal has a human immunoglobulin variable region.

In some embodiments, the instant invention relates to a method of identifying an antibody or antigen binding fragment thereof described herein that includes contacting an antibody or antigen binding fragment thereof with a polypeptide comprising an amino acid sequence of SEQ ID NO: 1, SEQ ID NO: 2 and/or SEQ ID NO: 3.24. In some embodiments the antibody or antigen binding fragment thereof is part of a library of antibodies or antigen binding fragments thereof.

In some embodiments, the instant invention relates to a method of treating prostate cancer, inhibiting angiogenesis and/or treating wet AMD in a subject (e.g., in a subject in need thereof) that includes the step of administering to the subject a therapeutically effective amount of a Plexin B2 antagonist (e.g., an antibody or antigen binding fragment thereof, an interfering nucleic acid, such as an siRNA, shRNA or antisense RNA, or a small molecule). In some embodiments the Plexin B2 antagonist inhibits the binding of ANG to Plexin B2 or the Plexin B2 mediated nuclear translocation of ANG. In some embodiments the Plexin B2 antagonist inhibits Plexin B2 protein expression.

In some embodiments the instant invention relates to an isolated nucleic acid encoding the heavy chain variable region and/or the light chain variable region of an antibody or antigen binding fragment thereof described herein. In some embodiments, the isolated nucleic acid is contained within a vector or a cell (e.g., a cell that expresses an antibody or antigen binding fragment thereof described herein).

In some embodiments the instant invention relates to an isolated nucleic acid encoding a polypeptide described herein. In some embodiments, the isolated nucleic acid is contained within a vector or a cell (e.g., a cell that expresses a polypeptide described herein).

In certain embodiments the instant invention relates to a kit containing an antibody, antigen binding fragment thereof, polypeptide and/or pharmaceutical composition described herein.

In some embodiments, the instant invention relates to a method of determining whether a test agent is a modulator (e.g., an inhibitor or an enhancer) of Plexin B2 activity. In certain embodiments, the method comprises forming a test reaction mixture that includes a Plexin B2 polypeptide or ANG-binding fragment thereof, an ANG polypeptide or Plexin B2-binding fragment thereof and a test agent. In some embodiments the method includes the step of incubating the test reaction mixture under conditions conducive for the formation of a complex between the Plexin B2 polypeptide or ANG-binding fragment thereof and the ANG polypeptide or Plexin B2-binding fragment thereof. In some embodiments, the method includes the step of determining the amount of the complex in the test reaction mixture. In some embodiments, a test agent that reduces the amount of the complex in the test reaction mixture compared to the amount of the complex in a control reaction mixture is an inhibitor of Plexin B2 activity. In certain embodiments, a test agent that increases the amount of complex in the test reaction mixture compared to the amount of the complex in a control reaction mixture is an enhancer of Plexin B2 activity.

In some embodiments, the Plexin-B2 polypeptide or ANG-binding fragment thereof comprises an amino acid sequence selected from the group consisting of SEQ ID NO: 1, SEQ ID NO: 2 and SEQ ID NO: 3. In some embodiments the ANG polypeptide or Plexin-B2 binding fragment thereof comprises an amino acid sequence of SEQ ID NO: 5.

In some embodiments the test agent is an antibody, a protein, a peptide or a small molecule. In certain embodiments the test agent is a member of a library of test agents.

In some embodiments, the control reaction mixture is substantially identical to the test reaction mixture except that the control reaction mixture does not comprise a test agent. In certain embodiments the control reaction mixture is substantially identical to the test reaction mixture except that the control reaction mixture comprises a placebo agent instead of a test agent.

In some embodiments, the test reaction mixture is formed by adding the test agent to a mixture comprising the Plexin B2 polypeptide or ANG-binding fragment thereof and the ANG polypeptide or Plexin B2-binding fragment thereof. In certain embodiments the test reaction mixture is formed by adding the Plexin B2 polypeptide or ANG-binding fragment thereof to a mixture comprising the test agent and the ANG polypeptide or Plexin B2-binding fragment thereof. In certain embodiments the test reaction mixture is formed by adding the ANG polypeptide or Plexin B2-binding fragment thereof to a mixture comprising the test agent and the Plexin B2 polypeptide or ANG-binding fragment thereof.

In certain embodiments, the Plexin B2 polypeptide or ANG-binding fragment thereof is anchored to a solid support in the test reaction mixture. In some embodiments the test reaction mixture is incubated under conditions conducive to the binding of the ANG polypeptide or Plexin B2-binding fragment thereof to the anchored Plexin B2 polypeptide or ANG-binding fragment thereof. In some embodiments, the method also includes the step of isolating ANG polypeptide or Plexin B2-binding fragment thereof bound to the Plexin B2 polypeptide or ANG-binding fragment thereof from ANG polypeptide or Plexin B2-binding fragment thereof not bound to the Plexin B2 polypeptide or ANG-binding fragment thereof. In certain embodiments, the amount of complex in the test reaction mixture is determined by detecting the amount of ANG polypeptide or Plexin B2-binding fragment thereof bound to the Plexin B2 polypeptide or ANG-binding fragment thereof. In some embodiments the ANG polypeptide or Plexin B2-binding fragment thereof is linked (e.g. bound either directly or indirectly) to a detectable moiety (e.g., a fluorescent moiety, a luminescent moiety, a radioactive moiety, etc.).

In some embodiments, the ANG polypeptide or Plexin B2-binding fragment thereof is anchored to a solid support in the test reaction mixture. In some embodiments the test reaction mixture is incubated under conditions conducive to the binding of the Plexin B2 polypeptide or ANG-binding fragment thereof to the anchored ANG polypeptide or Plexin B2-binding fragment thereof. In certain embodiments the method also includes the step of isolating Plexin B2 polypeptide or ANG-binding fragment thereof bound to the ANG polypeptide or Plexin B2-binding fragment thereof from Plexin B2 polypeptide or ANG-binding fragment thereof not bound to the ANG polypeptide or Plexin B2-binding fragment thereof. In some embodiments the amount of complex in the test reaction mixture is determined by detecting the amount of Plexin B2 polypeptide or ANG-binding fragment thereof bound to the ANG polypeptide or Plexin B2-binding fragment thereof. In certain embodiments the Plexin B2 polypeptide or ANG-binding fragment thereof is linked to a detectable moiety.

In some embodiments, the instant invention relates to a method of determining whether a test agent is an inhibitor of Plexin B2 activity that includes contacting a polypeptide comprising an epitope having a sequence selected from the group consisting of SEQ ID NO: 1, SEQ ID NO: 2 or SEQ ID NO: 3 with a test agent and determining whether the test agent binds to the epitope; wherein a test agent that binds to the epitope is an inhibitor of Plexin B2 activity. In some embodiments the test agent is an antibody, a protein, a peptide or a small molecule. In certain embodiments the test agent is a member of a library of test agents.

In some embodiments the polypeptide is attached to a solid substrate. In some embodiments, the method also includes the step of isolating test agent that is bound to the epitope from test agent that is not bound to the epitope. In some embodiments the test agent is linked to a detectable moiety.

In some embodiments the test agent is attached to a solid substrate. In certain embodiments the method also includes the step of isolating polypeptide that is bound to the test agent from polypeptide that is not bound to the test agent. In some embodiments the polypeptide is linked to a detectable moiety. In certain embodiments the test agent is a member of a library of test agents.

BRIEF DESCRIPTION OF THE DRAWINGS

FIG. 1 shows the amino acid sequences of three ANG binding epitopes of Plexin B1 (identified as SEQ ID NO: 1, 2 and 3, respectively).

FIG. 2 shows the amino acid sequence of human Plexin B2 (SEQ ID NO: 4).

FIG. 3 shows the amino acid sequence of human ANG (SEQ ID NO: 5).

FIG. 6 shows the binding of ANG to LNCaP cells. (A) Subconfluent LNCaP cells were incubated with $^{125}$I-ANG at 4° C. for 30 min and bound ANG was determined by a gamma counter. (B) Scatchard plot of the results produced in experiment described in (A).

DETAILED DESCRIPTION

General

Figure 4:
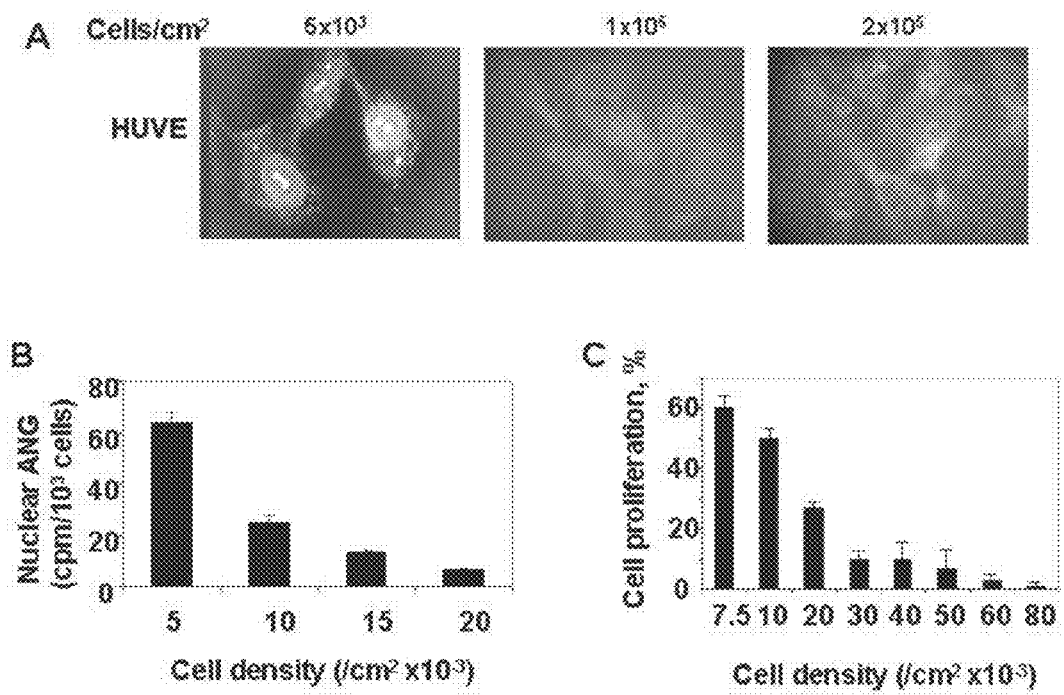
FIG. 4 shows that the nuclear translocation of ANG in endothelial cells is cell density dependent. (A) HUVE cells were cultured at the indicated density and incubated with 0.1 µg/ml ANG for 2 h. Nuclear ANG was detected by anti-ANG monoclonal antibody 26-2F and Alexa 488-labeled rabbit anti-mouse IgG antibody. (B) Nuclear translocation of $^{125}$I-ANG. $^{125}$I-ANG was incubated with HUVE cells cultured at different densities for 2 h. Nuclear fraction was isolated and the amount of $^{125}$I-ANG was determined by a gamma counter. (C). HUVE cells were cultured at the density indicated and incubated with 1 µg/ml ANG for 48 h. Cell numbers were determined by a Coulter counter.

Disclosed herein are novel compositions and methods for the treatment of cancer, the inhibition of angiogenesis and the treatment of angiogenesis-related diseases, such as wet AMD.

Angiogenin ("ANG") is an important mediator of blood vessel formation that has been implicated in the establishment, growth and metastasis of tumors. Unfortunately, development of therapies based on the inhibition of ANG's angiogenic and tumor promoting activities has been hampered by the fact that the ANG receptor was heretofore unknown.

As disclosed herein, the instant inventors discovered that Plexin B2 is an ANG receptor that mediates ANG's angiogenic and tumor promoting effects. As is also disclosed herein, the instant inventors identified positions where ANG binds to the Plexin B2 receptor and demonstrated that anti-Plexin B2 antibodies specific to these binding sites are able to inhibit the Plexin B2/ANG interaction and inhibit ANG activity.

Thus, in certain embodiments, the instant invention relates to compositions and/or methods for the treatment of ANG-related diseases or disorders (e.g., cancer or wet AMD) through the inhibition of Plexin B2. In some embodiments, the composition that inhibits Plexin B2 includes, for example, antibodies, antigen binding fragments thereof or polypeptides that bind to ANG or Plexin B2. Agents that inhibit the binding of ANG to Plexin B2 include, for example, antibodies or antigen binding fragments thereof that bind to an ANG binding epitope of Plexin B2 (e.g., an epitope containing an amino acid sequence of SEQ ID NO: 1, SEQ ID NO: 2 and/or SEQ ID NO: 3) and polypeptides that bind to ANG (e.g., polypeptides containing an amino acid sequence of SEQ ID NO: 1, SEQ ID NO: 2 and/or SEQ ID NO: 3).

DEFINITIONS

For convenience, certain terms employed in the specification, examples, and appended claims are collected here.

As used herein, the term "administering" means providing a pharmaceutical agent or composition to a subject, and includes, but is not limited to, administering by a medical professional and self-administering. Such an agent can contain, for example, a Plexin B2 antagonist such as an antibody, antigen binding fragment thereof or polypeptide described herein.

The term "agent" is used herein to denote a chemical compound, a small molecule, a mixture of chemical compounds and/or a biological macromolecule (such as a nucleic acid, an antibody, an antibody fragment, a protein or a peptide). Agents may be identified as having a particular activity by screening assays described herein below. The activity of such agents may render them suitable as a "therapeutic agent" which is a biologically, physiologically, or pharmacologically active substance (or substances) that acts locally or systemically in a subject.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

As used herein, the term "antibody" may refer to both an intact antibody and an antigen binding fragment thereof. Intact antibodies are glycoproteins that include at least two heavy (H) chains and two light (L) chains inter-connected by disulfide bonds. Each heavy chain includes a heavy chain variable region (abbreviated herein as $V_H$) and a heavy chain constant region. Each light chain includes a light chain variable region (abbreviated herein as $V_L$) and a light chain constant region. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The term "antibody" includes, for example, monoclonal antibodies, polyclonal antibodies, chimeric antibodies, humanized antibodies, human antibodies, multispecific antibodies (e.g., bispecific antibodies), single-chain antibodies and antigen-binding antibody fragments. An "isolated antibody," as used herein, refers to an antibody which is substantially free of other antibodies having different antigenic specificities. An isolated antibody may, however, have some cross-reactivity to other, related antigens.

The terms "antigen binding fragment" and "antigen-binding portion" of an antibody, as used herein, refers to one or more fragments of an antibody that retain the ability to bind to an antigen. Examples of binding fragments encompassed within the term "antigen-binding fragment" of an antibody include Fab, Fab', F(ab')$_2$, Fv, scFv, disulfide linked Fv, Fd, diabodies, single-chain antibodies, NANOBODIES®, isolated CDRH3, and other antibody fragments that retain at least a portion of the variable region of an intact antibody. These antibody fragments can be obtained using conventional recombinant and/or enzymatic techniques and can be screened for antigen binding in the same manner as intact antibodies.

The terms "CDR", and its plural "CDRs", refer to a complementarity determining region (CDR) of an antibody or antibody fragment, which determine the binding character of an antibody or antibody fragment. In most instances, three CDRs are present in a light chain variable region (CDRL1, CDRL2 and CDRL3) and three CDRs are present in a heavy chain variable region (CDRH1, CDRH2 and CDRH3). CDRs contribute to the functional activity of an antibody molecule and are separated by amino acid sequences that comprise scaffolding or framework regions. Among the various CDRs, the CDR3 sequences, and particularly CDRH3, are the most diverse and therefore have the strongest contribution to antibody specificity. There are at least two techniques for determining CDRs: (1) an approach based on cross-species sequence variability (i.e., Kabat et al., Sequences of Proteins of Immunological Interest (National Institute of Health, Bethesda, Md. (1987), incorporated by reference in its entirety); and (2) an approach based on crystallographic studies of antigen-antibody complexes (Chothia et al., Nature, 342:877 (1989), incorporated by reference in its entirety).

The term "epitope" means a protein determinant capable of specific binding to an antibody. Epitopes usually consist of chemically active surface groupings of molecules such as amino acids or sugar side chains. Certain epitopes can be defined by a particular sequence of amino acids to which an antibody is capable of binding, such as the sequences provided in SEQ ID NO: 1, SEQ ID NO: 2 and SEQ ID NO: 3.

As used herein, the term "humanized antibody" refers to an antibody that has at least one CDR derived from a mammal other than a human, and a FR region and the constant region of a human antibody. A humanized antibody is useful as an effective component in a therapeutic agent according to the present invention since antigenicity of the humanized antibody in human body is lowered.

The term "isolated polypeptide" refers to a polypeptide, in certain embodiments prepared from recombinant DNA or RNA, or of synthetic origin, or some combination thereof, which (1) is not associated with proteins that it is normally found with in nature, (2) is isolated from the cell in which it normally occurs, (3) is isolated free of other proteins from the same cellular source, (4) is expressed by a cell from a different species, or (5) does not occur in nature.

The term "isolated nucleic acid" refers to a polynucleotide of genomic, cDNA, or synthetic origin or some combination there of, which (1) is not associated with the cell in which the "isolated nucleic acid" is found in nature, or (2) is operably linked to a polynucleotide to which it is not linked in nature.

As used herein, the term "monoclonal antibody" refers to an antibody obtained from a population of substantially homogeneous antibodies that specifically bind to the same epitope, i.e., the individual antibodies comprising the population are identical except for possible naturally occurring mutations that may be present in minor amounts. The modifier "monoclonal" indicates the character of the antibody as being obtained from a substantially homogeneous population of antibodies, and is not to be construed as requiring production of the antibody by any particular method.

The terms "polynucleotide", and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component. The term "recombinant" polynucleotide means a polynucleotide of genomic, cDNA, semisynthetic, or synthetic origin which either does not occur in nature or is linked to another polynucleotide in a non-natural arrangement.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body As used herein, "specific binding" refers to the ability of an antibody to bind to a predetermined antigen or the ability of a polypeptide to bind to its predetermined binding partner. Typically, an antibody or polypeptide specifically binds to its predetermined antigen or binding partner with an affinity corresponding to a $K_D$ of about $10^{-7}$ M or less, and binds to the predetermined antigen/binding partner with an affinity (as expressed by $K_D$) that is at least 10 fold less, at least 100 fold less or at least 1000 fold less than its affinity for binding to a non-specific and unrelated antigen/binding partner (e.g., BSA, casein).

As used herein, the term "subject" means a human or non-human animal selected for treatment or therapy.

The phrases "therapeutically-effective amount" and "effective amount" as used herein means the amount of an agent which is effective for producing the desired therapeutic effect in at least a sub-population of cells in a subject at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented from worsening.

Anti-Plexin B2 Antibodies

In certain embodiments, the present invention relates to antibodies and antigen binding fragments thereof that bind specifically to Plexin B2 and uses thereof. In some embodiments, the antibodies bind to the epitope of Plexin B2 having an amino acid sequence of SEQ ID NO: 1, SEQ ID NO: 2 and/or SEQ ID NO: 3 and are therefore able to inhibit ANG binding to Plexin B2. Such antibodies can be polyclonal or monoclonal and can be, for example, murine, chimeric, humanized or fully human.

Polyclonal antibodies can be prepared by immunizing a suitable subject (e.g. a mouse) with a polypeptide immunogen (e.g., a polypeptide having a sequence of SEQ ID NO: 1, SEQ ID NO: 2 and/or SEQ ID NO: 3). The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well known techniques, such as protein A chromatography to obtain the IgG fraction.

At an appropriate time after immunization, e.g., when the antibody titers are highest, antibody-producing cells can be obtained from the subject and used to prepare monoclonal antibodies using standard techniques, such as the hybridoma technique originally described by Kohler and Milstein (1975) *Nature* 256:495-497) (see also Brown et al. (1981) *J. Immunol.* 127:539-46; Brown et al. (1980) *J. Biol. Chem.* 255: 4980-83; Yeh et al. (1976) *Proc. Natl. Acad. Sci.* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

As an alternative to preparing monoclonal antibody-secreting hybridomas, a monoclonal specific for Plexin B2 and/or a polypeptide having a sequence of SEQ ID NO: 1 can be identified and isolated by screening a recombinant combinatorial immunoglobulin library (e.g., an antibody phage display library or an antibody yeast display library) with the appropriate polypeptide (e.g. a polypeptide having a sequence of SEQ ID NO: 1) to thereby isolate immunoglobulin library members that bind the polypeptide.

Additionally, recombinant antibodies specific for Plexin B2 and/or a polypeptide having a sequence of SEQ ID NO: 1, such as chimeric or humanized monoclonal antibodies, can be made using standard recombinant DNA techniques. Such chimeric and humanized monoclonal antibodies can be produced by recombinant DNA techniques known in the art, for example using methods described in U.S. Pat. No. 4,816,567; U.S. Pat. No. 5,565,332; Better et al. (1988) *Science* 240: 1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *Biotechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

Human monoclonal antibodies specific for Plexin B2 and/or a polypeptide having a sequence of SEQ ID NO: 1, SEQ ID NO: 2 and/or SEQ ID NO: 3 can be generated using transgenic or transchromosomal mice carrying parts of the human immune system rather than the mouse system. For example, "HuMAb mice" which contain a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al. (1994) Nature 368(6474): 856 859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) Handbook of Experimental Pharmacology 113:49 101; Lonberg, N. and Huszar, D. (1995) Intern. Rev. Immunol. Vol. 13: 65 93, and Harding, F. and Lonberg, N. (1995) Ann. N.Y. Acad. Sci. 764:536 546). The preparation of HuMAb mice is described in Taylor, L. et al. (1992) Nucleic Acids Research 20:6287 6295; Chen, J. et al. (1993) International Immunology 5: 647 656; Tuaillon et al. (1993) Proc. Natl. Acad. Sci. USA 90:3720 3724; Choi et al. (1993) Nature Genetics 4:117 123; Chen, J. et al. (1993) EMBO J. 12: 821 830; Tuaillon et al. (1994) J. Immunol. 152:2912 2920; Lonberg et al., (1994) Nature 368(6474): 856 859; Lonberg, N. (1994) Handbook of Experimental Pharmacology 113:49 101; Taylor, L. et al. (1994) International Immunology 6: 579 591; Lonberg, N. and Huszar, D. (1995) Intern. Rev. Immunol. Vol. 13: 65 93; Harding, F. and Lonberg, N. (1995) Ann. N.Y. Acad. Sci. 764:536 546; Fishwild, D. et al. (1996) Nature Biotechnology 14: 845 851. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807.

In certain embodiments, the antibodies of the instant invention are able to bind to an epitope of Plexin B2 having an amino acid sequence of SEQ ID NO: 1, SEQ ID NO: 2 and/or SEQ ID NO: 3 with a dissociation constant of no greater than $10^{-6}$, $10^{-7}$, $10^{-8}$ or $10^{-9}$ M. Standard assays to evaluate the binding ability of the antibodies are known in the art, including for example, ELISAs, Western blots and RIAs. The binding kinetics (e.g., binding affinity) of the antibodies also can be assessed by standard assays known in the art, such as by Biacore analysis. In some embodiments, the binding of the antibody to Plexin B2 substantially inhibits the ability of ANG to bind to Plexin B2. As used herein, an antibody substantially inhibits binding of ANG to a Plexin B2 when an excess of polypeptide reduces the quantity of receptor bound to ligand by at least about 20%, 40%, 60% or 80%, 85% or 90% (as measured in an in vitro competitive binding assay).

Soluble Plexin B2 Receptor Polypeptides

In certain embodiments, the invention relates to isolated polypeptides comprising an ANG-binding epitope of Plexin B2 (i.e., comprising an amino acid sequence of SEQ ID NO: 1, SEQ ID NO: 2 and/or SEQ ID NO: 3). Such polypeptides can be useful, for example, for inhibiting ANG binding to Plexin B2 and for identifying and/or generating antibodies that specifically bind to the ANG-binding epitope of Plexin B2. In certain embodiments the polypeptide of the invention is not Plexin B2. In some embodiments the polypeptide of the invention comprises less than 100, 90, 80, 70, 60, 50, 40, 30, 25 or 20 consecutive amino acids of the natural Plexin B2 protein (e.g., a protein having an amino acid sequence of SEQ ID NO: 4). In some embodiments, the polypeptide of the invention consists of SEQ ID NO: 1, SEQ ID NO: 2 or SEQ ID NO: 3. In some embodiments, the polypeptide of the instant invention comprises amino acids 165-441 of the Plexin B2 amino acid sequence as set forth in SEQ ID NO: 4.

In some embodiments, the polypeptide of the instant invention is able to bind to ANG. In some embodiments, the polypeptide binds to ANG with a dissociation constant of no greater than $10^{-5}$ M, $10^{-6}$ M, $10^{-7}$ M, $10^{-8}$ M or $10^{-9}$ M. Standard assays to evaluate the binding ability of the polypeptides are known in the art, including for example, ELISAs, Western blots and RIAs and suitable assays are described in the Examples. The binding kinetics (e.g., binding affinity) of the polypeptides also can be assessed by standard assays known in the art, such as by Biacore analysis. In some embodiments, the binding of the polypeptide to ANG substantially inhibits the ability of ANG to bind to Plexin B2. As used herein, a polypeptide substantially inhibits adhesion of a ANG to a Plexin B2 when an excess of polypeptide reduces the quantity of receptor bound to ligand by at least about 20%, 40%, 60% or 80%, 85% or 90% (as measured in an in vitro competitive binding assay).

In some embodiments, the polypeptides of the present invention can be isolated from cells or tissue sources by an appropriate purification scheme using standard protein purification techniques. In another embodiment, polypeptides of the present invention are produced by recombinant DNA techniques. Alternatively, polypeptides of the present invention can be chemically synthesized using standard peptide synthesis techniques.

In some embodiments, polypeptides of the present invention comprise an amino acid sequence substantially identical SEQ ID NO: 1, SEQ ID NO: 2 and/or SEQ ID NO: 3. Accordingly, in another embodiment, the polypeptides of the present invention comprises an amino acid sequence at least about 80%, 85%, 90%, 91%, 92%, 93%, 94% or more identical to SEQ ID NO: 1, SEQ ID NO: 2 and/or SEQ ID NO: 3. In certain embodiments the polypeptides comprise an amino acid sequence at least about 80%, 85%, 90%, 91%, 92%, 93%, 94%, 95%, 96%, 97%, 98% or 99% identical to amino acids 165-441 of SEQ ID NO: 4.

In certain embodiments, the polypeptides of the present invention comprise an amino acid identical to SEQ ID NO: 1, SEQ ID NO: 2 and/or SEQ ID NO: 2 except for 1 or more (e.g., 1, 2, 3, 4, 5, 6, 7, 8, 9, 10 or more) conservative sequence modifications. As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues of the polypeptides described herein can be replaced with other amino acid residues from the same side chain family and the altered antibody can be tested for retained function using the functional assays described herein.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The invention also provides chimeric or fusion proteins. As used herein, a "chimeric protein" or "fusion protein" comprises a polypeptide(s) of the present invention (e.g., those comprising SEQ ID NO: 1, SEQ ID NO: 2 or SEQ ID NO: 3) linked to a distinct polypeptide to which it is not linked in nature. For example, the distinct polypeptide can be fused to the N-terminus or C-terminus of the polypeptide either directly, through a peptide bond, or indirectly through a chemical linker. In some embodiments, the peptide of the instant invention is linked to an immunoglobulin constant domain (e.g., an IgG constant domain, such as a human IgG constant domain).

A chimeric or fusion polypeptide of the present invention can be produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, Ausubel et al., eds., John Wiley & Sons: 1992). Moreover, many expression vectors are commercially available that already encode a fusion moiety.

The polypeptides described herein can be produced in prokaryotic or eukaryotic host cells by expression of polynucleotides encoding a polypeptide(s) of the present invention. Alternatively, such peptides can be synthesized by chemical methods. Methods for expression of heterologous polypeptides in recombinant hosts, chemical synthesis of polypeptides, and in vitro translation are well known in the art and are described further in Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) J. Am. Chem. Soc. 91:501; Chaiken I. M. (1981) CRC Crit. Rev. Biochem. 11:255; Kaiser et al. (1989) Science 243:187; Merrifield, B. (1986) Science 232:342; Kent, S. B. H. (1988) Annu Rev. Biochem. 57:957; and Offord, R. E. (1980) Semisynthetic Proteins, Wiley Publishing, which are incorporated herein by reference.

Inhibitory RNA Molecules

In certain embodiments, inhibitory RNA molecules that specifically target Plexin B2 mRNA (e.g., antisense molecules, siRNA or shRNA molecules, ribozymes or triplex molecules) are used in methods of the invention. Such molecules are useful, for example, in methods of inhibiting angiogenesis, treating wet AMD and/or treating cancer, including prostate cancer.

The inhibitory RNA molecules of the invention may be contacted with a cell or administered to an organism. Alternatively, constructs encoding these may be contacted with or introduced into a cell or organism. Antisense constructs, antisense oligonucleotides, RNA interference constructs or siRNA duplex RNA molecules can be used to interfere with expression of a protein of interest, e.g., a Plexin B2 protein. Typically at least 15, 17, 19, or 21 nucleotides of the complement of the Plexin B2 mRNA sequence (e.g. SEQ ID NO: 4) are sufficient for an antisense molecule. Typically at least 19, 21, 22, or 23 nucleotides of a target sequence are sufficient for an RNA interference molecule. The RNA interference molecule may have a 2 nucleotide 3' overhang. If the RNA interference molecule is expressed in a cell from a construct, for example from a hairpin molecule or from an inverted repeat of the desired Plexin B2 sequence, then the endogenous cellular machinery will create the overhangs. Inhibitory RNA molecules can be prepared by chemical synthesis, in vitro transcription, or digestion of long dsRNA by Rnase III or Dicer. These can be introduced into cells by transfection, electroporation, or other methods known in the art. See Hannon, G J, 2002, RNA Interference, Nature 418: 244-251; Bernstein E et al., 2002, The rest is silence. RNA 7: 1509-1521; Hutvagner G et al., RNAi: Nature abhors a double-strand. Curr. Opin. Genetics & Development 12: 225-232; Brummelkamp, 2002, A system for stable expression of short interfering RNAs in mammalian cells. Science 296: 550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. Nature Biotechnol. 20:500-505; Miyagishi M, and Taira K. (2002). U6-promoter-driven siRNAs with four uridine 3' overhangs efficiently suppress targeted gene expression in mammalian cells. Nature Biotechnol. 20:497-500; Paddison P J, Caudy A A, Bernstein E, Hannon G J, and Conklin D S. (2002). Short hairpin RNAs (shRNAs) induce sequence-specific silencing in mammalian cells. Genes & Dev. 16:948-958; Paul C P, Good P D, Winer I, and Engelke D R. (2002). Effective expression of small interfering RNA in human cells. Nature Biotechnol. 20:505-508; Sui G, Soohoo C, Affar E-B, Gay F, Shi Y, Forrester W C, and Shi Y. (2002). A DNA vector-based RNAi technology to suppress gene expression in mammalian cells. Proc. Natl. Acad. Sci. USA 99(6):5515-5520; Yu J-Y, DeRuiter S L, and Turner D L. (2002). RNA interference by expression of short-interfering RNAs and hairpin RNAs in mammalian cells. Proc. Natl. Acad. Sci. USA 99(9):6047-6052.

Antisense or RNA interference molecules can be delivered in vitro to cells or in vivo, e.g., to tumors or hypoxic tissues of a mammal. Typical delivery means known in the art can be used. For example, an interfering RNA can be delivered systemically using, for example, the methods and compositions described in PCT Application No: PCT/US09/036,223, PCT/US09/061,381 PCT/US09/063,927, PCT/US09/063,931 and PCT/US09/063,933, each of which is hereby incorporated by reference in its entirety. In certain embodiments the siRNA is delivered locally. For example, when the siRNA described herein is used to treat cancer, delivery to a tumor can be accomplished by intratumoral injections, as described, for example, in Takahashi et al., *Journal of Controlled Release* 116:90-95 (2006) and Kim et al., *Journal of Controlled Release* 129:107-116 (2008), each of which is incorporated by reference in its entirety. Alternatively, when the interfering RNA described herein is used to treat wet AMD, the interfering RNA can be delivered directly to the eye as described, for example, in Reich et al., *Mol. Vis.*, 9:210-216 (2003), which is incorporated by reference in its entirety.

Nucleic Acid Molecules

Another aspect of the invention pertains to nucleic acid molecules that encode the antibodies, antigen binding fragments thereof and/or polypeptides described herein. The nucleic acids may be present, for example, in whole cells, in a cell lysate, or in a partially purified or substantially pure form.

Nucleic acids of the invention can be obtained using standard molecular biology techniques. For example, nucleic acid molecules described herein can be cloned using standard PCR techniques or chemically synthesized. For nucleic acids encoding antibodies expressed by hybridomas, cDNAs encoding the light and/or heavy chains of the antibody made by the hybridoma can be obtained by standard PCR amplification or cDNA cloning techniques. For antibodies obtained from an immunoglobulin gene library (e.g., using phage or yeast display techniques), nucleic acid encoding the antibody can be recovered from the library.

Once DNA fragments encoding a $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

In certain embodiments, the instant invention relates to vectors that contain the isolated nucleic acid molecules described herein. As used herein, the term "vector," refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby be replicated along with the host genome. Moreover, certain vectors are capable of directing the expression of genes. Such vectors are referred to herein as "recombinant expression vectors" (or simply, "expression vectors").

In certain embodiments, the instant invention relates to cells that contain a nucleic acid described herein (e.g., a nucleic acid encoding an antibody, antigen binding fragment thereof or polypeptide described herein). The cell can be, for example, prokaryotic, eukaryotic, mammalian, avian, murine and/or human. In certain embodiments the cell is a hybridoma. In certain embodiments the nucleic acid of the invention is operably linked to a transcription control element such as a promoter. In some embodiments the cell transcribes the nucleic acid of the invention and thereby expresses an antibody, antigen binding fragment thereof or polypeptide described herein. The nucleic acid molecule can be integrated into the genome of the cell or it can be extrachromasomal.

Other Inhibitors of Plexin B2

Certain embodiments of the present invention relate to methods of inhibiting angiogenesis and/or preventing or treating prostate cancer or wet AMD. These methods include administering an agent that decreases the activity and/or expression of Plexin B2, and/or prevents the binding of Plexin B2 to ANG. Agents which may be used to modulate the activity of Plexin B2 include antibodies (e.g., antibodies that bind to SEQ ID NO: 1, SEQ ID NO: 2 or SEQ ID NO: 3), proteins, peptides, small molecules and inhibitory RNA molecules, e.g., siRNA molecules, shRNA, ribozymes, and antisense oligonucleotides specific for Plexin B2.

In some embodiments, any agent that modulates Plexin B2 can be used to practice the methods of the invention. Such agents can be those described herein, those known in the art, or those identified through routine screening assays (e.g. the screening assays described herein).

In some embodiments, assays used to identify agents useful in the methods of the present invention include a reaction between Plexin B2 and one or more assay components. The other components may be either a test compound (e.g. the potential agent), or a combination of test compounds and ANG. Agents identified via such assays, may be useful, for example, for preventing or treating prostate cancer or wet AMD and/or of inhibiting angiogenesis.

Agents useful in the methods of the present invention may be obtained from any available source, including systematic libraries of natural and/or synthetic compounds. Agents may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of agents may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

Agents useful in the methods of the present invention may be identified, for example, using assays for screening candidate or test compounds which modulate the activity of Plexin B2. For example, candidate or test compounds can be screened for the ability to inhibit the binding or Plexin B2 to ANG.

The basic principle of the assay systems used to identify compounds that modulate the activity of Plexin B2 involves preparing a reaction mixture containing Plexin B2 and ANG under conditions and for a time sufficient to allow Plexin B2 to bind to ANG. In order to test an agent for modulatory activity, the reaction mixture is prepared in the presence and absence of the test compound. The test compound can be initially included in the reaction mixture, or can be added at a time subsequent to the addition of Plexin B2 and ANG. Control reaction mixtures are incubated without the test compound or with a placebo. The formation of any complexes between Plexin B2 and ANG is then detected. The formation of a complex in the control reaction, but less or no such formation in the reaction mixture containing the test compound, indicates that the compound interferes with the interaction of Plexin B2 and ANG.

The assay for compounds that modulate the interaction of Plexin B2 with ANG may be conducted in a heterogeneous or homogeneous format. Heterogeneous assays involve anchoring either Plexin B2 or ANG onto a solid phase and detecting complexes anchored to the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between Plexin B2 and ANG (e.g., by competition) can be identified by conducting the reaction in the presence of the test substance, i.e., by adding the test substance to the reaction mixture prior to or simultaneously with Plexin B2 and ANG. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either Plexin B2 or ANG is anchored onto a solid surface or matrix, while the other corresponding non-anchored component may be labeled, either directly or indirectly. In practice, microtitre plates are often utilized for this approach. The anchored species can be immobilized by a number of methods, either non-covalent or covalent, that are typically well known to one who practices the art. Non-covalent attachment can often be accomplished simply by coating the solid surface with a solution of Plexin B2 or ANG and drying. Alternatively, an immobilized antibody specific for the assay component to be anchored can be used for this purpose.

In related assays, a fusion protein can be provided which adds a domain that allows one or both of the assay components to be anchored to a matrix. For example, glutathione-S-transferase/marker fusion proteins or glutathione-S-transferase/binding partner can be adsorbed onto glutathione sepharose beads (Sigma Chemical, St. Louis, Mo.) or glutathione derivatized microtiter plates, which are then combined with the test compound or the test compound and either the non-adsorbed Plexin B2 or ANG, and the mixture incubated under conditions conducive to complex formation (e.g., physiological conditions). Following incubation, the beads or microtiter plate wells are washed to remove any unbound assay components, the immobilized complex assessed either directly or indirectly, for example, as described above. Alternatively, the complexes can be dissociated from the matrix, and the level of Plexin B2 binding or activity determined using standard techniques.

A homogeneous assay may also be used to identify inhibitors of Plexin B2. This is typically a reaction, analogous to those mentioned above, which is conducted in a liquid phase in the presence or absence of the test compound. The formed complexes are then separated from unreacted components, and the amount of complex formed is determined. As mentioned for heterogeneous assay systems, the order of addition of reactants to the liquid phase can yield information about which test compounds modulate (inhibit or enhance) complex formation and which disrupt preformed complexes.

In such a homogeneous assay, the reaction products may be separated from unreacted assay components by any of a number of standard techniques, including but not limited to: differential centrifugation, chromatography, electrophoresis and immunoprecipitation. In differential centrifugation, complexes of molecules may be separated from uncomplexed molecules through a series of centrifugal steps, due to the different sedimentation equilibria of complexes based on their different sizes and densities (see, for example, Rivas, G., and Minton, A. P., *Trends Biochem Sci* 1993 August; 18(8): 284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the complex as compared to the uncomplexed molecules may be exploited to differentially separate the complex from the remaining individual reactants, for example through the use of ion-exchange chromatography resins. Such resins and chromatographic techniques are well known to one skilled in the art (see, e.g., Heegaard, 1998, *J Mol. Recognit.* 11:141-148; Hage and Tweed, 1997, *J. Chromatogr. B. Biomed. Sci. Appl.*, 699:499-525). Gel electrophoresis may also be employed to separate complexed molecules from unbound species (see, e.g., Ausubel et al (eds.), In: *Current Protocols in Molecular Biology*, J. Wiley & Sons, New York. 1999). In this technique, protein or nucleic acid complexes are separated based on size or charge, for example. In order to maintain the binding interaction during the electrophoretic process, nondenaturing gels in the absence of reducing agent are typically preferred, but conditions appropriate to the particular interactants will be well known to one skilled in the art. Immunoprecipitation is another common technique utilized for the isolation of a protein-protein complex from solution (see, e.g., Ausubel et al (eds.), In: *Current Protocols in Molecular Biology*, J. Wiley & Sons, New York. 1999). In this technique, all proteins binding to an antibody specific to one of the binding molecules are precipitated from solution by conjugating the antibody to a polymer bead that may be readily collected by centrifugation. The bound assay components are released from the beads (through a specific proteolysis event or other technique well known in the art which will not disturb the protein-protein interaction in the complex), and a second immunoprecipitation step is performed, this time utilizing antibodies specific for the correspondingly different interacting assay component. In this manner, only formed complexes should remain attached to the beads. Variations in complex formation in both the presence and the absence of a test compound can be compared, thus offering information about the ability of the compound to modulate interactions between Plexin B2 and ANG.

Modulators of Plexin B2 expression may also be identified, for example, using methods wherein a cell is contacted with a candidate compound and the expression of Plexin B2 mRNA or protein is determined. The level of expression of mRNA or protein in the presence of the candidate compound is compared to the level of expression of mRNA or protein in the absence of the candidate compound. The candidate compound can then be identified as an inhibitor of Plexin B2 expression based on this comparison.

Pharmaceutical Compositions

In certain embodiments the instant invention relates to a composition, e.g., a pharmaceutical composition, containing at least one antibody, antigen binding fragment thereof or ANG binding polypeptide described herein formulated together with a pharmaceutically acceptable carrier. In one embodiment, the composition includes a combination of multiple (e.g., two or more) agents of the invention.

Pharmaceutical compositions of the invention also can be administered in combination therapy, i.e., combined with other agents. For example, the pharmaceutical composition of the invention may also include additional angiogenesis inhibitors, such as Bevacizumab (Avastin®) ranibizumab (Lucentis®) and Aflibercept (VEGF Trap).

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; or (2) parenteral administration, for example, by subcutaneous, intramuscular, intravenous or epidural injection as, for example, a sterile solution or suspension, or sustained-release formulation.

Methods of preparing these formulations or compositions include the step of bringing into association an agent described herein with the carrier and, optionally, one or more accessory ingredients. In general, the formulations are prepared by uniformly and intimately bringing into association an agent described herein with liquid carriers, or finely divided solid carriers, or both, and then, if necessary, shaping the product.

Pharmaceutical compositions of this invention suitable for parenteral administration comprise one or more agents described herein in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Regardless of the route of administration selected, the agents of the present invention, which may be used in a suitable hydrated form, and/or the pharmaceutical compositions of the present invention, are formulated into pharmaceutically-acceptable dosage forms by conventional methods known to those of skill in the art.

Therapeutic Methods

Disclosed herein are novel therapeutic methods of treatment or prevention of ANG-related conditions, including cancer (e.g., prostate cancer or brain cancer, such as glioblastoma) and wet AMD, and/or the inhibition of angiogenesis.

In some embodiments, the present invention provides therapeutic methods of treating cancer, including a cancerous tumor (e.g., a solid tumor) comprising administering to a subject, (e.g., a subject in need thereof), an effective amount of an agent that inhibits Plexin B2 expression or activity or inhibits the binding of ANG to Plexin B2. In some embodiments the present invention provides therapeutic methods of inhibiting angiogenesis or treating angiogenesis-mediated diseases, including wet AMD or cancer.

The pharmaceutical compositions of the present invention may be delivered by any suitable route of administration, including orally, nasally, as by, for example, a spray, rectally, intravaginally, parenterally, intracisternally and topically, as by powders, ointments or drops, including buccally and sublingually. In certain embodiments the pharmaceutical compositions are delivered generally (e.g., via oral or parenteral administration). In certain other embodiments the pharmaceutical compositions are delivered locally through direct injection into a tumor (in the case of a cancer treatment) or direct injection into the eye (in the case of a wet AMD treatment).

When used for treating cancer, such methods may comprise administering pharmaceutical compositions described herein in conjunction with one or more chemotherapeutic agents and/or angiogenesis inhibitors, including, for example, Bevacizumab (Avastin®) ranibizumab (Lucentis®) and Aflibercept (VEGF Trap).

Conjunctive therapy includes sequential, simultaneous and separate, and/or co-administration of the active compounds in a such a way that the therapeutic effects of the first agent administered have not entirely disappeared when the subsequent agent is administered. In certain embodiments, the second agent may be co-formulated with the first agent or be formulated in a separate pharmaceutical composition.

In certain embodiments, the present invention relates to the therapeutic methods of treating wet AMD that include administering to a subject (e.g., a subject in need thereof), an effective amount of an agent described herein. A subject in need thereof may include, for example, a subject who has been diagnosed with wet AMD, a subject predisposed to wet AMD or a subject who has been treated for wet AMD, including subjects that have been refractory to the previous treatment.

In certain embodiments, the present invention provides therapeutic methods of treating cancer, including a cancerous tumor (e.g., a solid tumor) comprising administering to a subject, (e.g., a subject in need thereof), an effective amount of an agent described herein. A subject in need thereof may include, for example, a subject who has been diagnosed with a tumor, including a pre-cancerous tumor, a cancer, or a subject who has been treated, including subjects that have been refractory to the previous treatment.

The methods of the present invention may be used to treat any cancerous or pre-cancerous tumor. In certain embodiments, the cancerous tumor is prostate cancer or brain cancer (e.g., glioblastoma). Cancers that may treated by methods and compositions of the invention also include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the compounds of the invention employed in the pharmaceutical composition at levels lower than that required in order to achieve the desired therapeutic effect and gradually increase the dosage until the desired effect is achieved.

EXEMPLIFICATION

The invention now being generally described will be more readily understood by reference to the following examples which are included merely for purposes of illustration of certain aspects and embodiments of the present invention, and are not intended to limit the invention in any way.

Example 1

Cell Density-Dependent Expression of ANG Receptor in Endothelial Cells but not in Prostate Cancer Cells Because ANG was originally identified as an angiogenic protein, previous efforts have focused on endothelial cells. However, as described herein, the activity of ANG on endothelial cells is strictly dependent on cell density (FIG. 4). Immunofluorescence showed that nuclear translocation of exogenous ANG in human umbilical vein endothelial (HUVE) cells occurs only in sparsely cultured cells (FIG. 4A). Nuclear translocation decreased as cell density increased and ceased in confluent cells. Cell density-dependent nuclear translocation of ANG in HUVE cells was confirmed with the use of $^{125}$I-labeled ANG as shown in FIG. 4B. Consistently, ANG-induced HUVE cell proliferation was also dependent on cell density (FIG. 4C). The inverse correlation of ANG activity toward endothelial cells to cell density indicates that the ANG receptor is down-regulated in endothelial cells when cell density increases.

Figure 5:
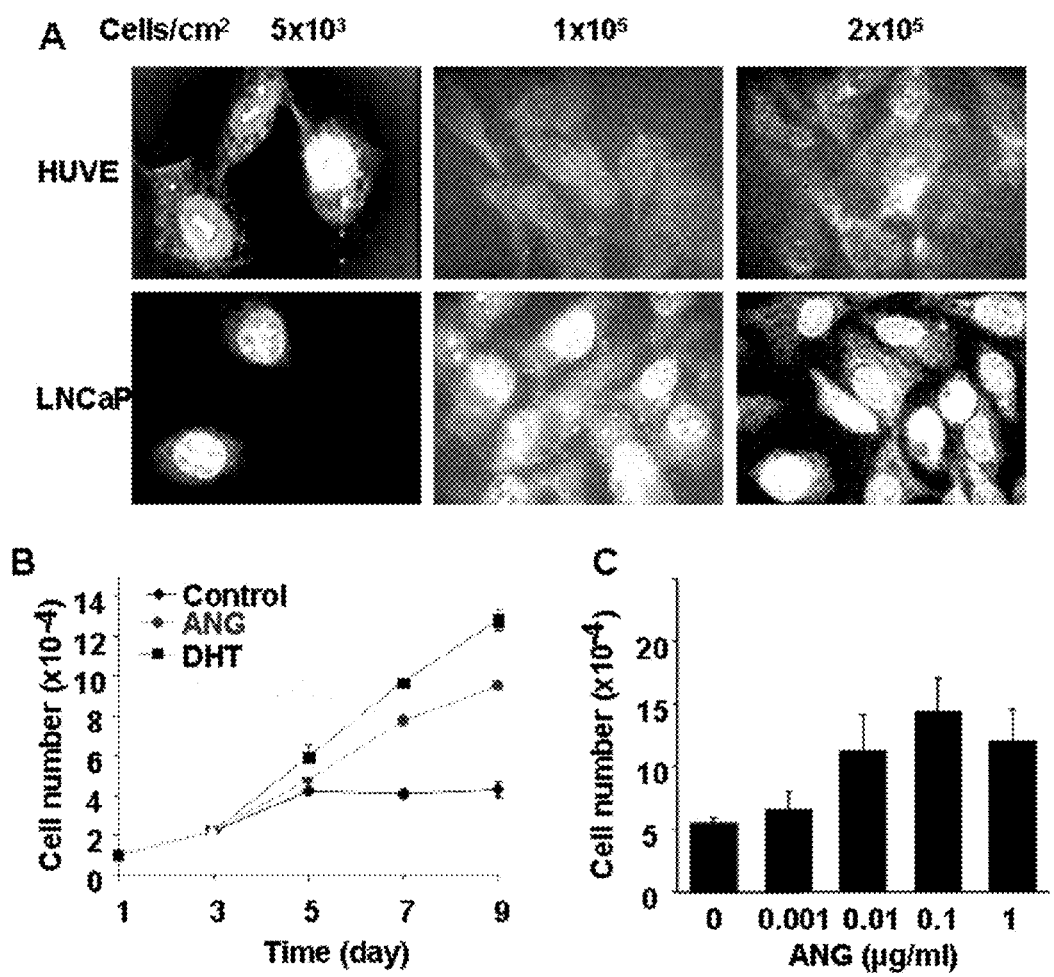
FIG. 5 shows the effect of ANG on LNCaP cells. (A) HUVE and LNCaP cells were cultured at the density indicated, and incubated with 0.1 µg/ml ANG for 2 h. Nuclear ANG were detected by indirect immunofluorescence with 26-2F and Alex 488 labeled 2nd antibody. (B) LNCaP cells were culture in phenol red-free and charcoal/dextran-stripped (steroid-free) FBS for 2 day and stimulated with DHT (10 nM), ANG (0.1 µg/ml), or a mixture of the two for the time indicated. (C) Dose dependence. ANG was added to the cells and cultured for 4 days. Cell numbers were determined with a Coulter counter.

Human ANG is upregulated in human prostate cancer, especially in androgen-independent prostate cancer. Mouse ANG is the highest upregulated gene in AKT-induced prostate intraepithelial neoplasia (PIN) tissue in the murine prostate-restricted AKT kinase transgenic (MPAKT) mice. ANG plays a dual role in prostate cancer progression. It not only mediates tumor angiogenesis but also directly stimulates cancer cell proliferation. As described herein, in contrast to endothelial cells, nuclear translocation of ANG in LNCaP human prostate cancer cells is not dependent on cell density (FIG. 5A). Normally, LNCaP cells will survive but will not proliferate when cultured in phenol red-free and steroid-free medium (FIG. 5B). Dihydrotestosterone (DHT) stimulated LNCaP cell proliferation as shown in FIG. 5B. ANG also stimulated LNCaP cell proliferation in the absence of androgen, indicating that ANG can compensate for androgen-deprivation. No additive or synergistic effect was observed when ANG and DHT are added simultaneously, indicating that ANG and DHT share the same mechanism in stimulating LNCaP cell proliferation. FIG. 5C shows that ANG stimulated LNCaP cell proliferation in a dose-dependent manner. These results indicate that ANG receptor is expressed in LNCaP cells and that the expression of ANG receptor is not down-regulated in LNCaP cells when cell density increase.

Example 2

Identification of Plexin B2 as an ANG Binding Protein

The thermodynamics of ANG binding to LNCaP cells was determined by a standard radio receptor assay. ANG was labeled with iodine-125 and incubated with ANG receptor expressing LNCaP cells at 4° C. FIG. 6A shows that the binding of $^{125}$I-ANG to LNCaP cells is saturable. Scatchard analysis identified two ANG binding sites with the apparent Kd of 0.45 nM and 170 nM, respectively (FIG. 6B).

Figure 7:
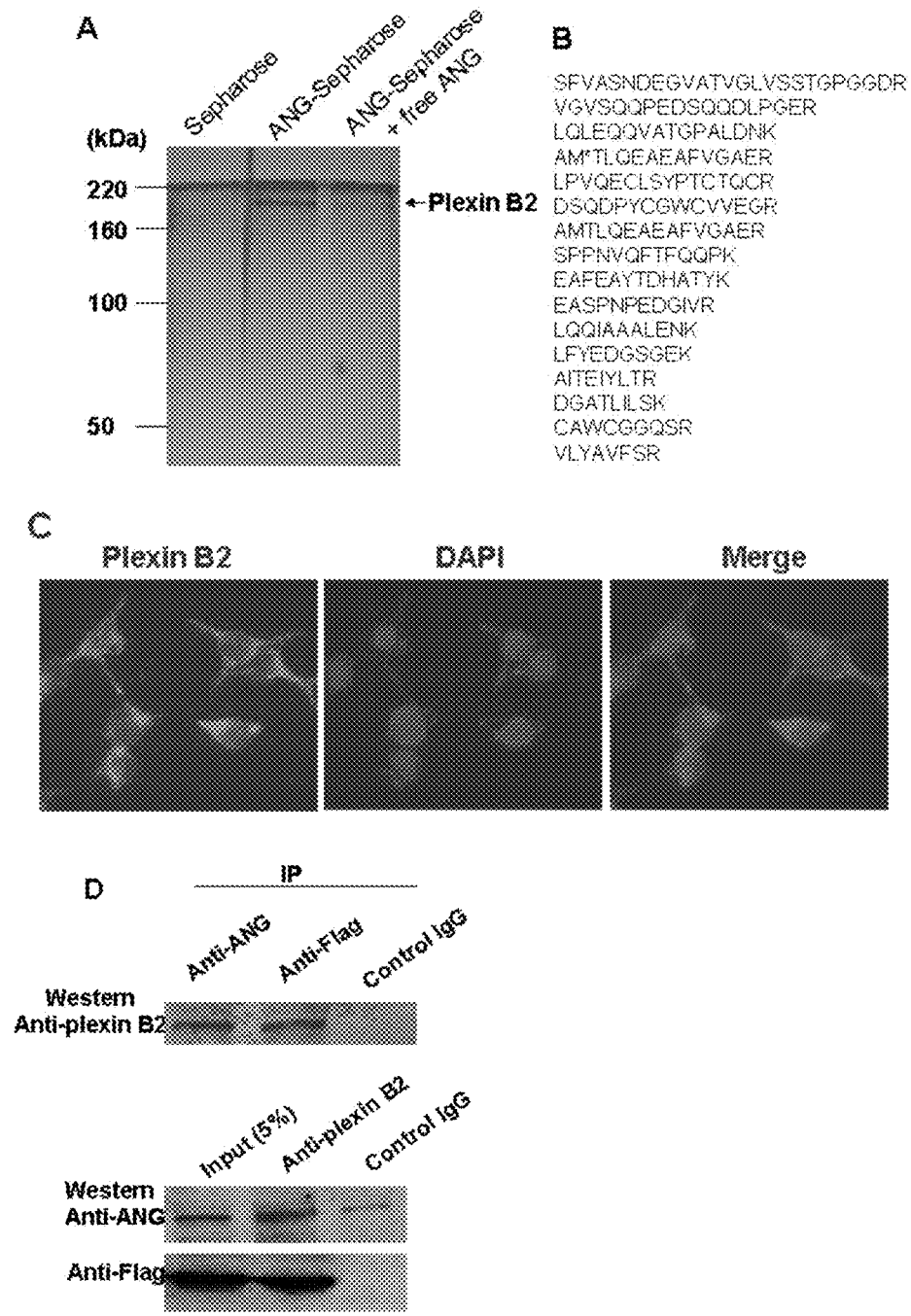
FIG. 7 shows that Plexin B2 is an ANG binding molecule. (A) Plasma membranes from a total of 2.5×10$^8$ LNCaP cells were prepared, solubilized and passed through an RNase A-Sepharose column to remove non-specific proteins. The flow through fraction from the RNase A column was divided in three equal fractions and applied to a non-affinity Sepharose column, an ANG-Sepharose column, and an ANG-Sepharose column after incubation with 0.1 mg free ANG, respectively. The bound materials were eluted with a low pH buffer and separated on an SDS-PAGE. (B) The band in the middle lane of the left panel was excised, digested with trypsin and subjected to Mass Spec determination of the molecular weight of the peptides. A total of 16 peptides (SEQ ID NOs: 6-21, respectively) were shown to be matched to Plexin B2. (C) Plexin B2 was detected by immunofluorescence with a goat anti-human Plexin B2 antibody (Santa Cruz sc-34507, 5 µg/ml), and the nuclei were stained by DAPI (middle panel). (D) Flag tagged (C-terminus) ANG was incubated with solubilized plasma membrane of LNCaP cells at RT for 30 min. The ANG-Plexin B2 complex was immunoprecipitated by anti-ANG mAb 26-2F or anti-Flag IgG and detected by Anti-Plexin B2 IgG (upper panel). In another experiment, the complex was precipitated with anti-Plexin B2 IgG and detected with anti-ANG pAB R113 (lower panel).

Affinity chromatography on an ANG-Sepharose column was used to isolate a putative ANG receptor. Plasma membranes from a total of $2.5 \times 10^8$ LNCaP cells were prepared, solublized and passed through an RNase A-Sepharose column to remove non-specific proteins (RNase A and ANG have 35% amino acid identity with an overall homology of 56%. However, RNase A is not angiogenic and does not bind to the LNCaP cell surface). The flow-through fraction from the RNase A column was divided in three equal fractions and applied to a non-affinity Sepharose column, an ANG-Sepharose column, and an ANG-Sepharose column after incubation with 0.1 mg free ANG, respectively. The bound materials were eluted with a low pH buffer and separated on SDS-PAGE. As shown in FIG. 7A, a prominent band with the apparent MW of ~200 kDa was eluted from ANG-Sepharose column (middle lane). This band did not appear in the eluate from the non-affinity Sepharose column (left lane) and its abundance was greatly reduced when the samples were pre-incubated with free ANG (right lane), indicating it was specific for ANG.

This band was excised from the gel and the tryptic peptides were submitted for Mass Spectrometry analysis. A Mascot search of the NCBInr database revealed a total of 16 matches to the peptides of human Plexin B2 (FIG. 7B). Plexin B2 is a cell surface protein mainly expressed in cells of neuronal origin. Plexin family proteins interact with Semaphorin to modulate neuronal migration and pattern formation, as well as angiogenesis, invasive growth, and apoptosis.

The expression of Plexin B2 in LNCaP cells was examined by immunofluorescence. As shown in FIG. 7C, Plexin B2 was detected mainly on the cell surface, consistent with it being a transmembrane protein. In order to know whether ANG associates with Plexin B2 in vivo, a co-immunoprecipitation experiment was performed. For this purpose, a flag tag was added to the C-terminus of ANG and the fusion protein was prepared and purified from an *E. Coli* expression system. ANG-Flag was incubated with the solublized plasma membrane fraction of LNCaP cells and subjected to IP-Western analysis. Plexin B2 can be precipitated both by anti-ANG monoclonal antibody as well as by anti-Flag antibody (FIG. 7D, upper panel). Similarly, ANG can be precipitated by anti-Plexin B2 antibody (FIG. 7D, lower panel). These results confirmed that ANG can indeed bind to Plexin B2.

Example 3

Plexin B2 Mediates the Nuclear Translocation of ANG

Figure 8:
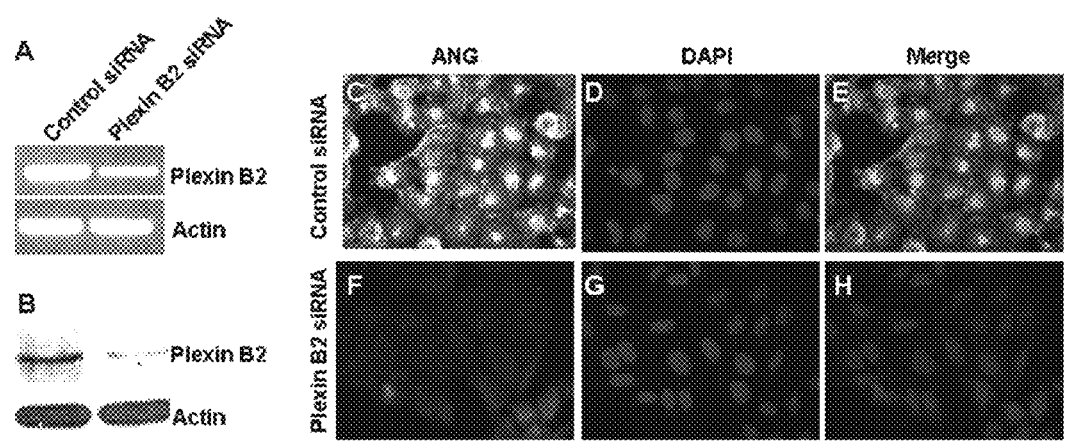
FIG. 8 shows that Plexin B2 specific siRNA inhibits nuclear translocation of ANG in LNCaP cells. LNCaP cells were transfected with control or Plexin B2 specific siRNA (Santa Cruz) at the final concentration of 60 nM. (A) RT-PCR analysis of Plexin B2 mRNA in control and siRNA transfected cells (48 h after transfection). (B) Western blotting detection of Plexin B2 protein (72 h after transfection). (C—H) LNCaP cells were transfected with control and Plexin B2 siRNA in the presence of lipofectamine 2000 for 72 h, and then incubated with 1 ug/ml ANG for 2 h. ANG was detected by immunofluorescence (C and F), and nuclei were stained by DAPI (D and G). The merged images were shown in E and H.

Synthetic siRNA was used to knock down Plexin B2 expression in LNCaP cells (FIG. 8). The knockdown efficiency was determined by both RT-PCR (FIG. 8A) and Western blotting (FIG. 8B) analyses. FIG. 8C shows that nuclear translocation of ANG in LNCaP cells was inhibited in Plexin B2 knockdown cells (FIG. 8F). These results demonstrated that Plexin B2 is essential for nuclear translocation of ANG.

Figure 9:
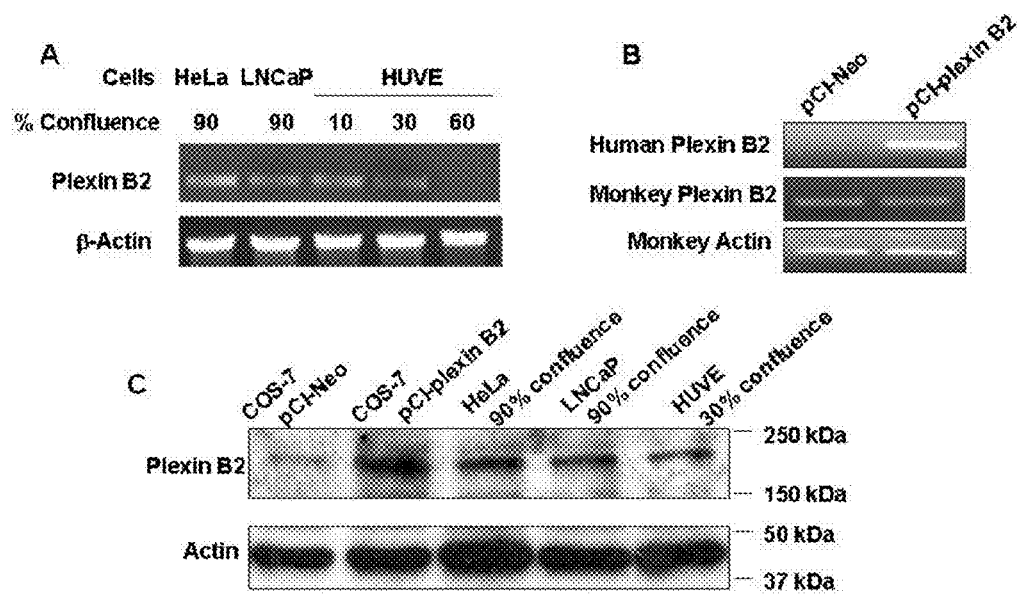
FIG. 9 shows Plexin B2 expression in HeLa, LNCaP, HUVE and COS-7 cells. (A) RT-PCR analyses of Plexin B2 mRNA in HeLa, LNCaP, and HUVE cells cultured at the density indicated. (B) The full length of human Plexin B2 cDNA was cloned into pCI-Neo vector and transfected into COS-7 cells. Stable transfectants were selected and analyzed for human (transgene) and Monkey (endogenous) Plexin B2 mRNA by RT-PCR. (C) Western blotting analysis of Plexin B2 protein with goat-anti human Plexin B2 antibody that also recognizes monkey protein.

As described above, nuclear translocation of ANG is cell density dependent in endothelial cells but is constitutive in cancer cells (FIG. 4). The expression level of Plexin B2 in HUVE cells cultured under different density was therefore examined. FIG. 9A shows that Plexin B2 mRNA was detectable in HUVE cells when the cells were at 10% confluence. The expression was decreased in 30% confluent cells and was diminished when the confluence reached 60%. In contrast, Plexin B2 mRNA was still detectable in 90% confluent HeLa and LNCaP cells (FIG. 9A). These results are consistent with Plexin B2 being a functional receptor for ANG.

In order to further characterize the function of Plexin B2 in mediating the activity of ANG, the full length Plexin B2 cDNA was cloned into a pCI-neo vector which was transfected into COS-7 cells. Stable transfectants of the vector control (pCI-neo) and Plexin B2 (pCI-Plexin B2) were selected and the transgene expression was detected by RT-PCR analysis with a primer set that is specific to human Plexin B2 (FIG. 9B). Low level of monkey Plexin B2 mRNA was detected in both vector and Plexin B2 transfectants (FIG. 9B). Western blotting with an anti-Plexin B2 IgG showed a low level of Plexin B2 protein in vector transfectants of COS-7 cells and an increased level in Plexin B2 transfectants (FIG. 9C). Plexin B2 protein was also detected in 90% confluent HeLA and LNCaP cells and in 30% confluent HUVE cells (FIG. 9C).

Figure 10:
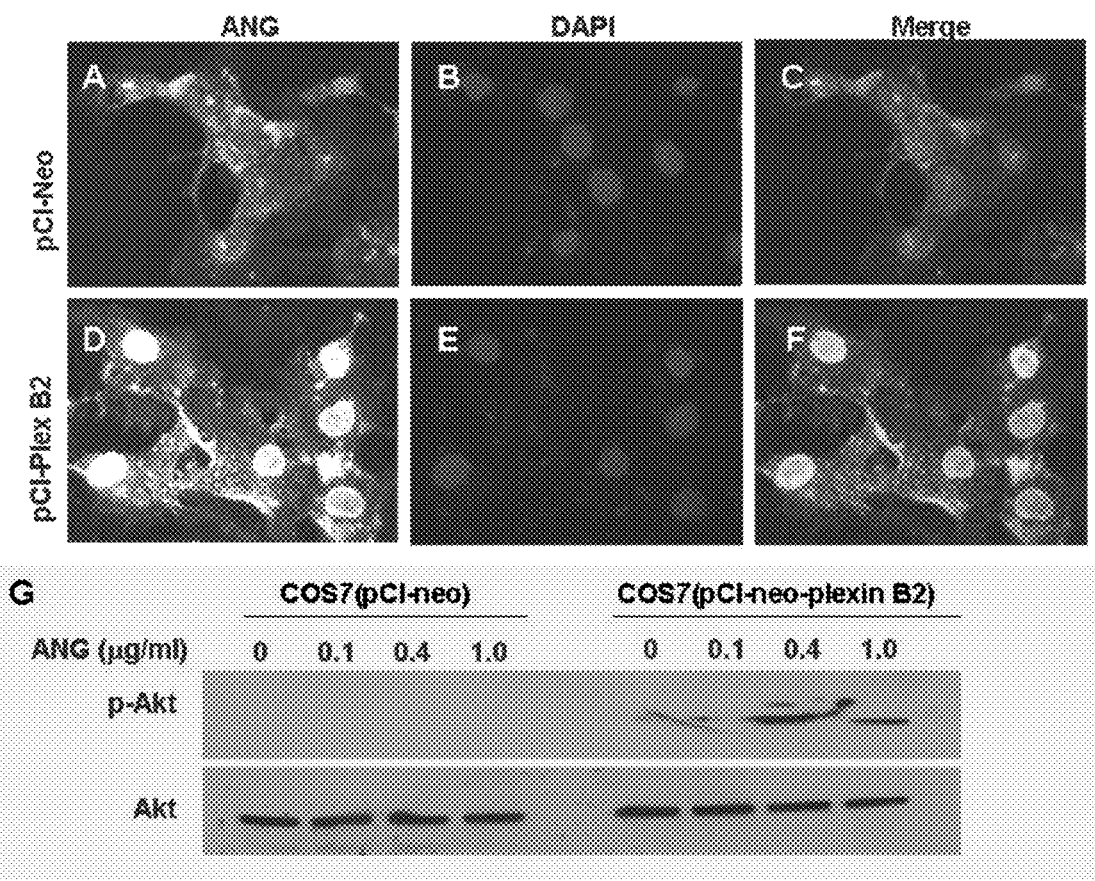
FIG. 10 shows the nuclear translocation of ANG in COS-7 cells transfected with Plexin B2 cDNA. Vector (A-C) and Plexin B2 (D-F) transfected COS-7 cells were incubated with 1 µg/ml ANG for 2 h. ANG was detected by immunofluorescence (A and D). Nuclei were stained by DAPI (B and E). The merged images were shown in C and F. (G) Vector and Plexin B2 transfectants were incubated with ANG at the concentration indicated for 2 h. Cells were lysed, cell lysates (60 µg protein) were subjected for SDS-PAGE and Western analysis for phospho-AKT and total AKT with respective antibodies.

Next, nuclear translocation of ANG in vector and Plexin B2 transfectants of COS-7 cells were examined. FIG. 10 shows that robust nuclear translocation occurred in Plexin B2 transfectants but only a minimum amount of nuclear ANG was detected in vector transfectants. Therefore, the expression of human Plexin B2 in COS-7 cells enables nuclear translocation of ANG, indicating that Plexin B2 is sufficient to mediate nuclear translocation of ANG.

ANG has been shown to activate AKT in endothelial cells. The phosphorylation status of AKT in the Plexin B2 transfectants of COS-7 cells was examined. FIG. 10G shows that ANG treatment induced AKT phosphorylation in Plexin B2 transfectants of COS-7 cells but not in vector control transfectants. These results suggest that Plexin B2 is a functional receptor for ANG and is responsible for mediating both nuclear translocation of ANG and AKT phosphorylation.

Figure 11:
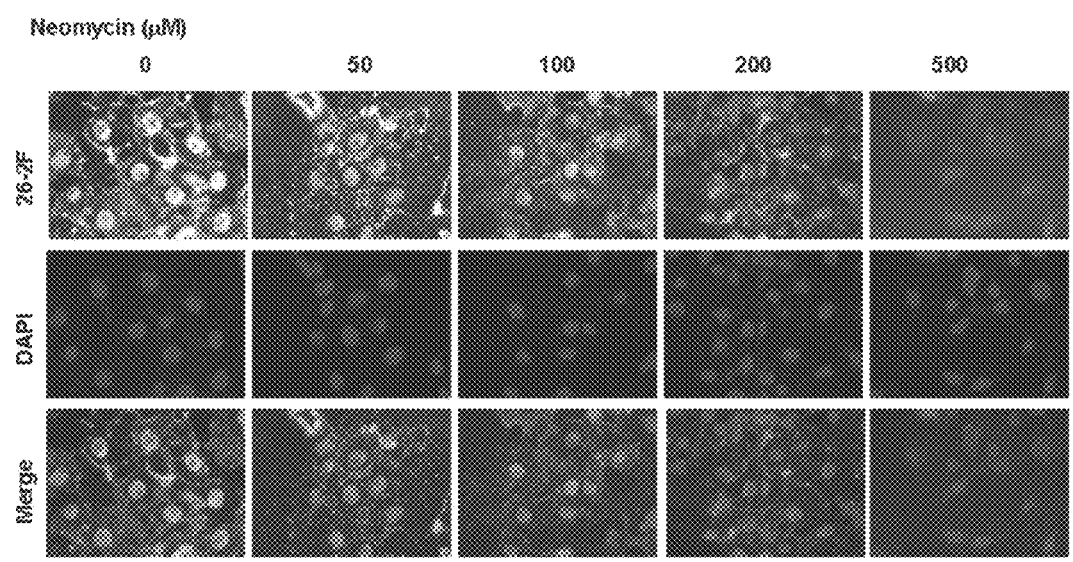
FIG. 11 shows that neomycin inhibits nuclear translocation of ANG in Plexin B2-transfected COS-7 cells. The Plexin B2 transfectants were treated with neomycin at the concentration indicated for 10 min and then incubated with 1 µg/ml ANG for 2 h. ANG was detected by immunofluorescence (top panels). Nuclei were stained by DAPI (middle panels). The merged images were shown in bottom panels.

Neomycin has been shown to block nuclear translocation of ANG in endothelial cells and in cancer cells. The effect of neomycin on Plexin B2 transfectants of COS-7 cells was examined. FIG. 11 shows that neomycin inhibits nuclear translocation of ANG in the Plexin B2 transfectants of COS-7 cells in a dose-dependent manner. Therefore, transfection of human Plexin B2 cDNA converted COS-7 cells into ANG responsive cells. In term of nuclear translocation of ANG, which is essential for the biological activity of ANG, Plexin B2 transfectants of COS-7 cells act in a similar fashion as do LNCaP cells and sparsely cultured HUVE cells, the two known ANG responsive cell lines.

Example 4

Mapping of ANG Binding Domain on Plexin B2

Figure 12:
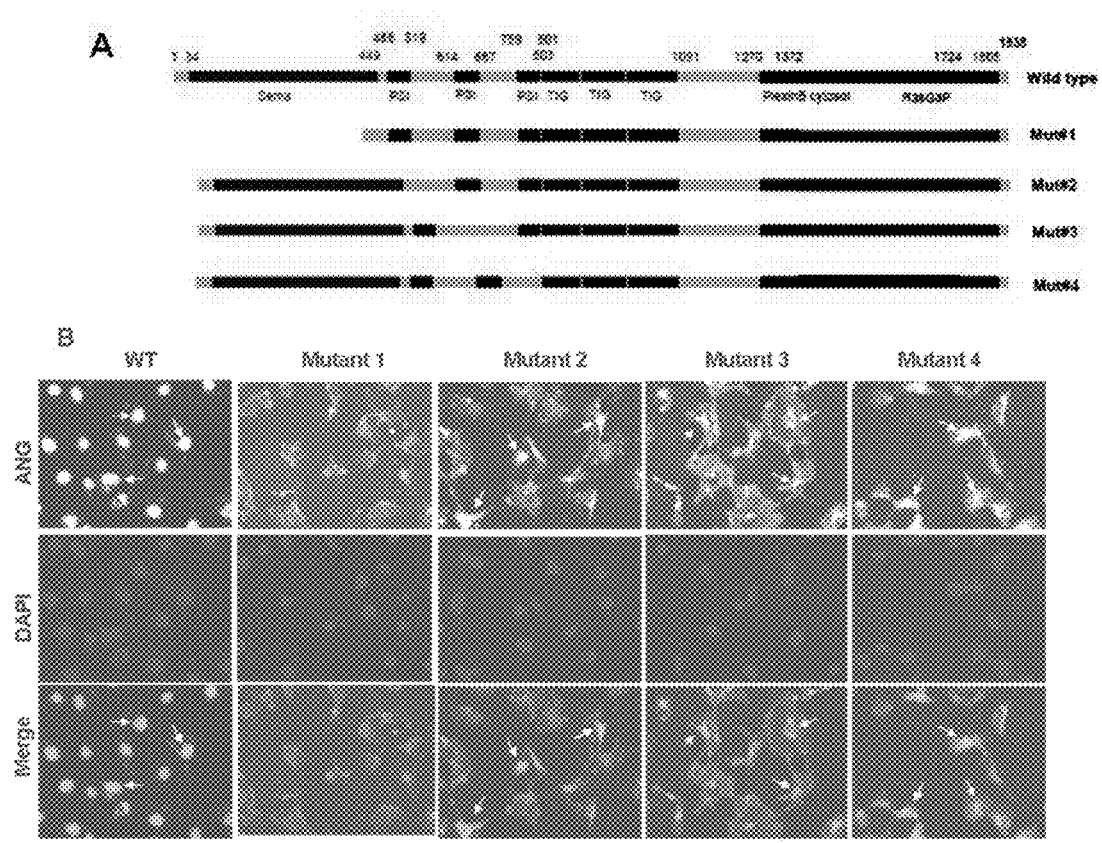
FIG. 12 shows the identification of the ANG binding domain. (A) Gene structures of the WT Plexin B2 and deletion mutants. (B) Nuclear translocation of ANG in various Plexin B2 transfectants of COS-7 cells. WT Plexin B2 cDNA or different deletion mutants were constructed in pCI-Neo vectors and transfected into COS-7 cells. The transfectants were incubated with 1 µg/ml ANG for 2 min. ANG was detected by immunofluorescence (top panels). Nuclei were stained by DAPI (middle panels). The merged images were shown in the bottom panel. Representative nuclear staining of ANG was indicated by arrows.

Plexin B2 is a single passing transmembrane protein with a large extracellular portion and a relatively small intracellular domain (FIG. 12A). The extracellular portion is composed of a Sema domain, 3 PSI domain, and 3 TIG domains. In order to determine the ANG binding site, a series of deletion mutants were made in which either the Sema domain or one of the 3 PSI domains have been deleted (FIG. 12A). These deletion mutants were transfected into COS-7 cells and nuclear translocation of ANG in these transfectants was determined by immunofluorescence. As shown in FIG. 12B, nuclear translocation of ANG still occurred in COS-7 cells transfected with mutants 2, 3, and 4 but not in mutant 1 transfected cells, indicating that ANG binds to the Sema domain of Plexin B2. By this method, the putative binding site for ANG was located at between residues 316 and 449 of the Plexin B2 amino acid sequence. A series of peptides of 18 amino acids covering this region were chemically synthesized and their binding affinity to ANG protein was examined by ELISA as well as by equilibrium dialysis. it was found that peptides having the amino acid sequence GTSSEYDSIL-VEINKRVK (SEQ ID NO: 1), LDKVHAKMEANRNAC (SEQ ID NO: 2) and RDGLRGTAVLQRGGLNL (SEQ ID NO: 3) were able to bind to ANG, indicating that these amino acid sequences are the ANG binding epitopes of Plexin B2.

Example 5

Figure 13:
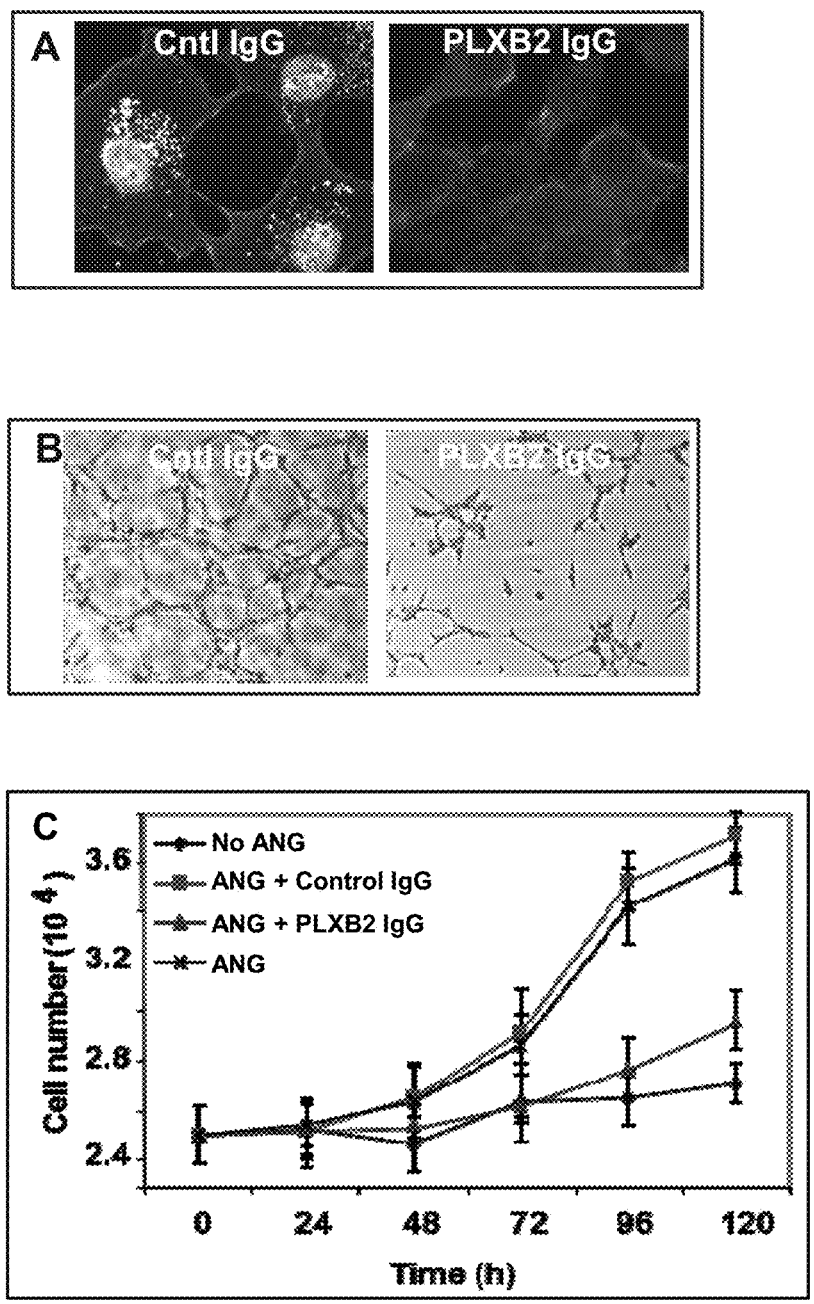
FIG. 13 shows that ant-Plexin B2 antibody inhibits ANG activity. (A) Anti-Plexin B2 antibody inhibits nuclear translocation of ANG in LNCaP cells. (B) Anti-Plexin B2 antibody inhibits ANG-induced angiogenesis in HUVEC tube formation assay. (C) Anti-Plexin B2 antibody inhibits ANG-induced LNCaP cell proliferation.

Antibodies Specific to the ANG Binding Epitope of Plexin B2 Inhibit ANG Activity This ANG binding peptide sequence represented by SEQ ID NO: 1, which bound ANG with an apparent Kd of 0.2 µM, was used to generate a polyclonal anti-Plexin B2 antibody as described herein. FIG. 10A shows that treatment of LNCaP cells with this affinity-purified anti-PlexinB2 antibody blocks nuclear translocation of ANG, whereas a nonimmune IgG has no effect on nuclear translocation of ANG (FIG. 13A). Similarly, the anti-Plexin B2 antibody inhibited ANG-induced endothelial tube formation (FIG. 13B) as well as LNCaP cell proliferation (FIG. 13C).

Example 6

Enhanced Plexin B2 Expression in Prostate Cancer Tissues

Figure 14:
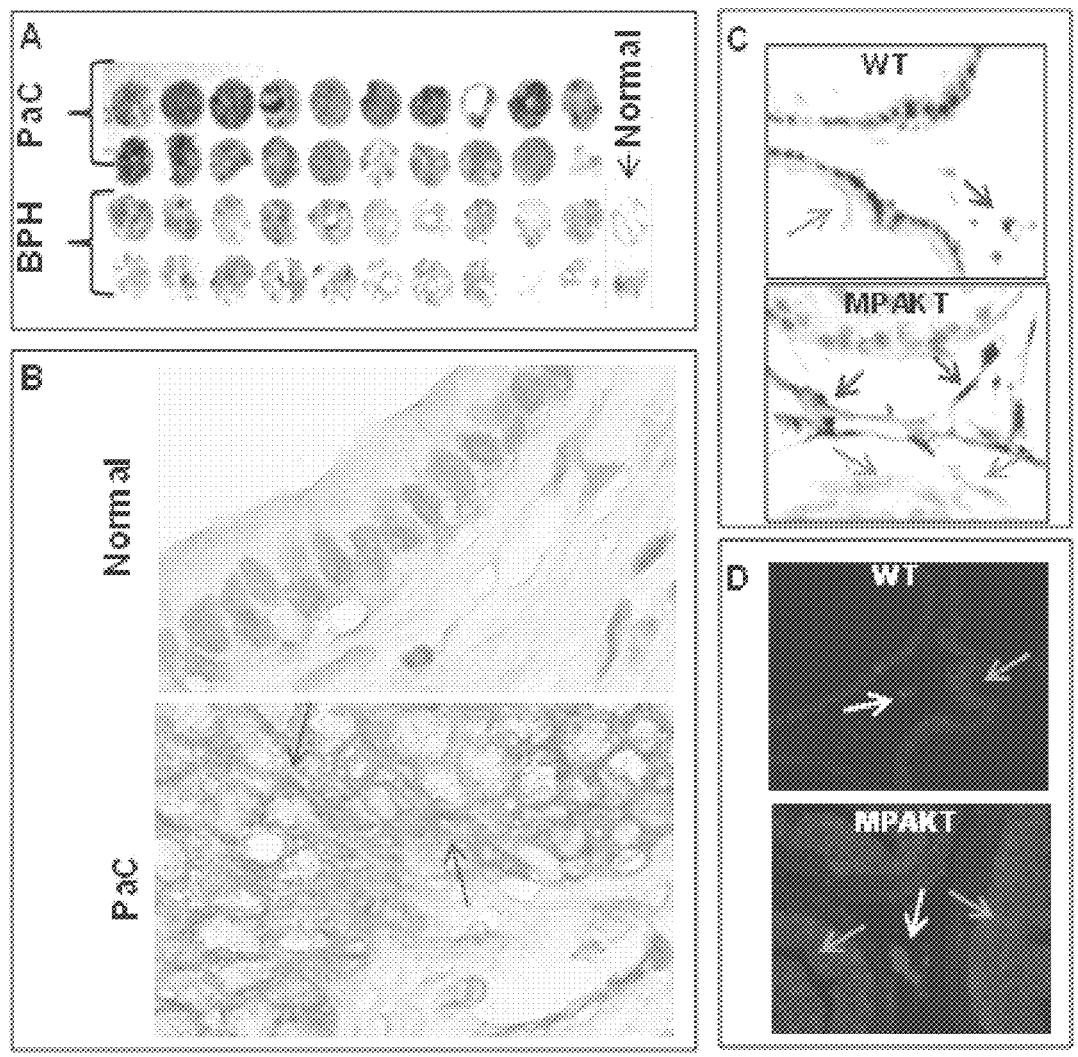
FIG. 14 shows enhanced Plexin B2 expression in prostate cancer. (A) IHC staining of Plexin B2 in human prostate cancer (top 2 rows), BPH (bottom 2 rows), and normal prostate (right) tissues. (B) High magnification images of human Plexin B2 staining in normal and prostate cancer samples. (C and D) IHC and IF staining of mouse Plexin B2 in the prostates from WT and MPAKT mice.

The expression level of Plexin B2 was examined in both human and mouse cancer tissues. FIG. 14A depicts the IHC staining of Plexin B2 in a human prostate tissue array. The cancer tissues (top 2 rows) had significantly stronger staining than the benign prostate hyperplasia (BPH) (bottom 2 rows). The 2 normal prostate tissues samples on the array (far right) had no or very weak staining FIG. 14B depicts high magnification images of normal and prostate cancer tissue. Plexin B2 was located on the cell surface of cancer cells (arrows). Plexin B2 was also overexpressed in the PIN tissues of MPAKT mice (FIGS. 14C and 14D). Both IHC and IF show that Plexin B2 was strongly expressed in the endothelial cells of the inter-glandular blood vessels (arrows in FIG. 14C and FIG. 14D) as well as in glandular epithelial cells of the PIN tissue, but was expressed very weakly in WT mice.

Example 7

Antibodies to the ANG Binding Epitope of Plexin B2 Inhibit Tumor Growth in Mice

Figure 15:
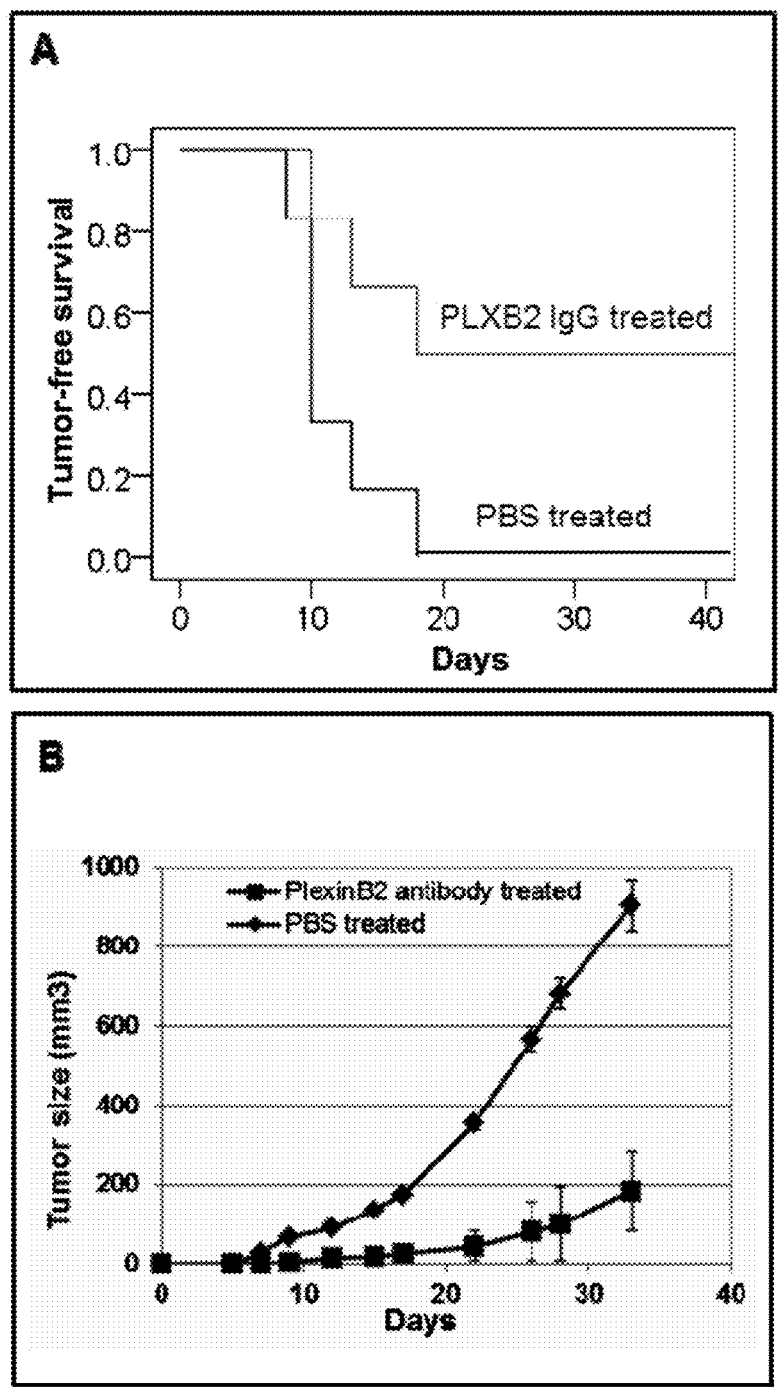
FIG. 15 shows enhanced anti-Plexin B2 inhibits tumor growth in mice. (A) Graph depicting tumor-free survival athymic mice transplanted with PC-3 cell tumors treated daily with s.c. injection of 60 µg/mouse of PlexinB2 polyclonal antibody or PBS control. (B) Graph depicting tumor size in athymic mice transplanted with PC-3 described in (A). (C) Photographs of the athymic mice transplanted with PC-3 described in (A). (D) Photographs of the dissected tumors taken from the athymic mice transplanted with PC-3 described in (A).
Figure 15:
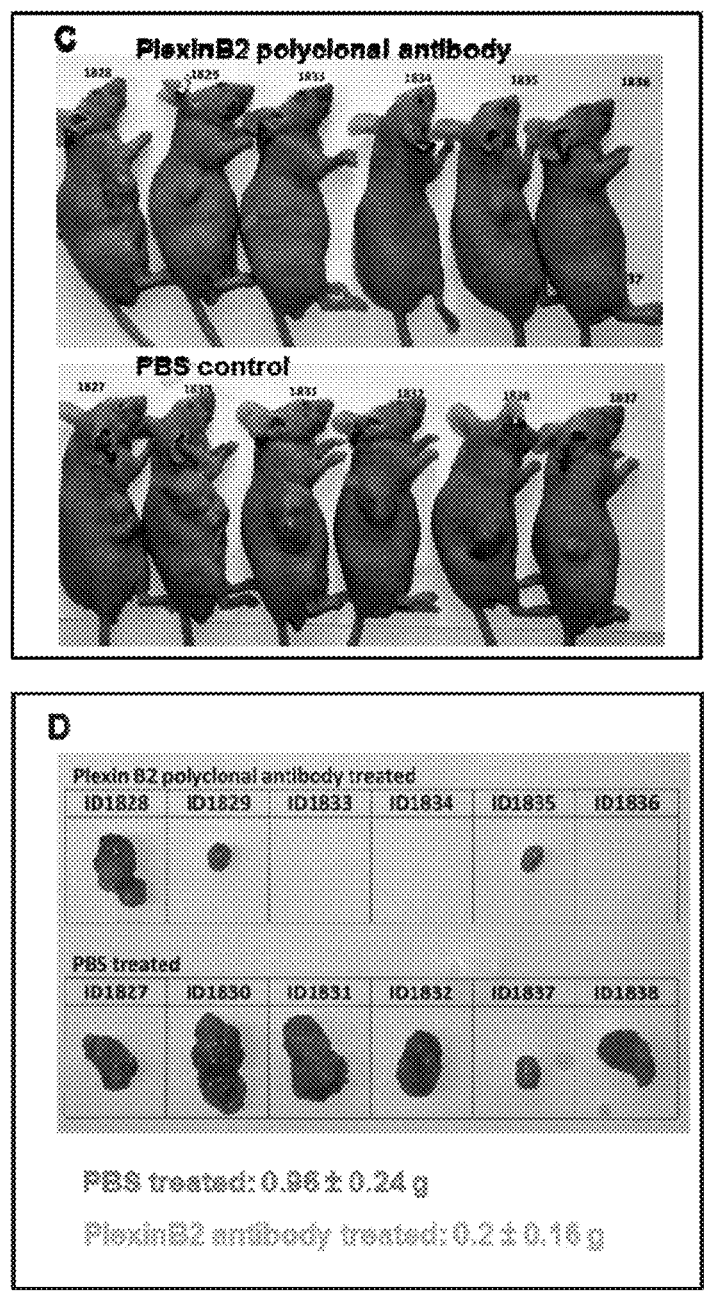

The inhibitory activity of the Plexin B2 antibody described above against xenograft growth of PC-3 cell tumors in athymic mice were investigated. Daily treatment of s.c. injection of 60 µg/mouse of Plexin B2 antibody prevented the establishment of PC-3 cell tumors by 50% ($1 \times 10^6$ cells in 100 µl volume containing 33 µl Matrigel) (FIG. 15A). All of the mice (n=6) in the control group (PBS treatment) developed palpable tumors by day 18. However, half of the Plexin B2 antibody-treated mice never developed tumors at the end of the experiment (day 40). Among the mice that did develop tumors, their growth rate is markedly slowed down (FIG. 15 B-D). The average tumor weight in PBS-treated and in PlexinB2 antibody-treated animals was 0.96±0.24 g and 0.2±0.16 g, respectively. Thus, PlexinB2 IgG inhibits PC-3 cell tumor growth in athymic mice by 79%.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated antibody or antigen binding fragment thereof that specifically binds to an Angiogenin (ANG) binding epitope of Plexin B2, wherein the ANG binding epitope consisting of an amino acid sequence of SEQ ID NO: 1, SEQ ID NO: 2 or SEQ ID NO: 3.

2. The antibody or antigen binding fragment thereof of claim 1, wherein the antibody or antigen binding fragment thereof inhibits the binding of Angiogenin to Plexin B2.

* * * * *

```
SEQUENCE LISTING

<160> NUMBER OF SEQ ID NOS: 21

<210> SEQ ID NO 1
<211> LENGTH: 18
<212> TYPE: PRT
<213> ORGANISM: Homo sapiens

<400> SEQUENCE: 1

Gly Thr Ser Ser Glu Tyr Asp Ser Ile Leu Val Glu Ile Asn Lys Arg
1               5                   10                  15

Val Lys

<210> SEQ ID NO 2
<211> LENGTH: 15
<212> TYPE: PRT
<213> ORGANISM: Homo sapiens

<400> SEQUENCE: 2

Leu Asp Lys Val His Ala Lys Met Glu Ala Asn Arg Asn Ala Cys
1               5                   10                  15

<210> SEQ ID NO 3
<211> LENGTH: 17
<212> TYPE: PRT
<213> ORGANISM: Homo sapiens

<400> SEQUENCE: 3

Arg Asp Gly Leu Arg Gly Thr Ala Val Leu Gln Arg Gly Gly Leu Asn
1               5                   10                  15

Leu

<210> SEQ ID NO 4
<211> LENGTH: 1838
<212> TYPE: PRT
<213> ORGANISM: Homo sapiens

<400> SEQUENCE: 4

Met Ala Leu Gln Leu Trp Ala Leu Thr Leu Leu Gly Leu Leu Gly Ala
1               5                   10                  15

Gly Ala Ser Leu Arg Pro Arg Lys Leu Asp Phe Phe Arg Ser Glu Lys
                20                  25                  30

Glu Leu Asn His Leu Ala Val Asp Glu Ala Ser Gly Val Val Tyr Leu
            35                  40                  45

Gly Ala Val Asn Ala Leu Tyr Gln Leu Asp Ala Lys Leu Gln Leu Glu
        50                  55                  60

Gln Gln Val Ala Thr Gly Pro Ala Leu Asp Asn Lys Lys Cys Thr Pro
65                  70                  75                  80
```

-continued

```
Pro Ile Glu Ala Ser Gln Cys His Glu Ala Glu Met Thr Asp Asn Val
                85                  90                  95
Asn Gln Leu Leu Leu Leu Asp Pro Pro Arg Lys Arg Leu Val Glu Cys
            100                 105                 110
Gly Ser Leu Phe Lys Gly Ile Cys Ala Leu Arg Ala Leu Ser Asn Ile
        115                 120                 125
Ser Leu Arg Leu Phe Tyr Glu Asp Gly Ser Gly Glu Lys Ser Phe Val
    130                 135                 140
Ala Ser Asn Asp Glu Gly Val Ala Thr Val Gly Leu Val Ser Ser Thr
145                 150                 155                 160
Gly Pro Gly Gly Asp Arg Val Leu Phe Val Gly Lys Gly Asn Gly Pro
                165                 170                 175
His Asp Asn Gly Ile Ile Val Ser Thr Arg Leu Leu Asp Arg Thr Asp
            180                 185                 190
Ser Arg Glu Ala Phe Glu Ala Tyr Thr Asp His Ala Thr Tyr Lys Ala
        195                 200                 205
Gly Tyr Leu Ser Thr Asn Thr Gln Gln Phe Val Ala Ala Phe Glu Asp
    210                 215                 220
Gly Pro Tyr Val Phe Phe Val Phe Asn Gln Gln Asp Lys His Pro Ala
225                 230                 235                 240
Arg Asn Arg Thr Leu Leu Ala Arg Met Cys Arg Glu Asp Pro Asn Tyr
                245                 250                 255
Tyr Ser Tyr Leu Glu Met Asp Leu Gln Cys Arg Asp Pro Asp Ile His
            260                 265                 270
Ala Ala Ala Phe Gly Thr Cys Leu Ala Ala Ser Val Ala Ala Pro Gly
        275                 280                 285
Ser Gly Arg Val Leu Tyr Ala Val Phe Ser Arg Asp Ser Arg Ser Ser
    290                 295                 300
Gly Gly Pro Gly Ala Gly Leu Cys Leu Phe Pro Leu Asp Lys Val His
305                 310                 315                 320
Ala Lys Met Glu Ala Asn Arg Asn Ala Cys Tyr Thr Gly Thr Arg Glu
                325                 330                 335
Ala Arg Asp Ile Phe Tyr Lys Pro Phe His Gly Asp Ile Gln Cys Gly
            340                 345                 350
Gly His Ala Pro Gly Ser Ser Lys Ser Phe Pro Cys Gly Ser Glu His
        355                 360                 365
Leu Pro Tyr Pro Leu Gly Ser Arg Asp Gly Leu Arg Gly Thr Ala Val
    370                 375                 380
Leu Gln Arg Gly Gly Leu Asn Leu Thr Ala Val Thr Val Ala Ala Glu
385                 390                 395                 400
Asn Asn His Thr Val Ala Phe Leu Gly Thr Ser Asp Gly Arg Ile Leu
                405                 410                 415
Lys Val Tyr Leu Thr Pro Asp Gly Thr Ser Glu Tyr Asp Ser Ile
            420                 425                 430
Leu Val Glu Ile Asn Lys Arg Val Lys Arg Asp Leu Val Leu Ser Gly
        435                 440                 445
Asp Leu Gly Ser Leu Tyr Ala Met Thr Gln Asp Lys Val Phe Arg Leu
    450                 455                 460
Pro Val Gln Glu Cys Leu Ser Tyr Pro Thr Cys Thr Gln Cys Arg Asp
465                 470                 475                 480
Ser Gln Asp Pro Tyr Cys Gly Trp Cys Val Val Glu Gly Arg Cys Thr
                485                 490                 495
Arg Lys Ala Glu Cys Pro Arg Ala Glu Glu Ala Ser His Trp Leu Trp
```

```
            500                 505                 510
Ser Arg Ser Lys Ser Cys Val Ala Val Thr Ser Ala Gln Pro Gln Asn
            515                 520                 525

Met Ser Arg Arg Ala Gln Gly Glu Val Gln Leu Thr Val Ser Pro Leu
            530                 535                 540

Pro Ala Leu Ser Glu Glu Asp Glu Leu Leu Cys Leu Phe Gly Glu Ser
545                 550                 555                 560

Pro Pro His Pro Ala Arg Val Glu Gly Glu Ala Val Ile Cys Asn Ser
                565                 570                 575

Pro Ser Ser Ile Pro Val Thr Pro Pro Gly Gln Asp His Val Ala Val
            580                 585                 590

Thr Ile Gln Leu Leu Arg Arg Gly Asn Ile Phe Leu Thr Ser Tyr
            595                 600                 605

Gln Tyr Pro Phe Tyr Asp Cys Arg Gln Ala Met Ser Leu Glu Glu Asn
            610                 615                 620

Leu Pro Cys Ile Ser Cys Val Ser Asn Arg Trp Thr Cys Gln Trp Asp
625                 630                 635                 640

Leu Arg Tyr His Glu Cys Arg Glu Ala Ser Pro Asn Pro Glu Asp Gly
                645                 650                 655

Ile Val Arg Ala His Met Glu Asp Ser Cys Pro Gln Phe Leu Gly Pro
            660                 665                 670

Ser Pro Leu Val Ile Pro Met Asn His Glu Thr Asp Val Asn Phe Gln
            675                 680                 685

Gly Lys Asn Leu Asp Thr Val Lys Gly Ser Ser Leu His Val Gly Ser
            690                 695                 700

Asp Leu Leu Lys Phe Met Glu Pro Val Thr Met Gln Glu Ser Gly Thr
705                 710                 715                 720

Phe Ala Phe Arg Thr Pro Lys Leu Ser His Asp Ala Asn Glu Thr Leu
                725                 730                 735

Pro Leu His Leu Tyr Val Lys Ser Tyr Gly Lys Asn Ile Asp Ser Lys
            740                 745                 750

Leu His Val Thr Leu Tyr Asn Cys Ser Phe Gly Arg Ser Asp Cys Ser
            755                 760                 765

Leu Cys Arg Ala Ala Asn Pro Asp Tyr Arg Cys Ala Trp Cys Gly Gly
770                 775                 780

Gln Ser Arg Cys Val Tyr Glu Ala Leu Cys Asn Thr Thr Ser Glu Cys
785                 790                 795                 800

Pro Pro Pro Val Ile Thr Arg Ile Gln Pro Glu Thr Gly Pro Leu Gly
                805                 810                 815

Gly Gly Ile Arg Ile Thr Ile Leu Gly Ser Asn Leu Gly Val Gln Ala
            820                 825                 830

Gly Asp Ile Gln Arg Ile Ser Val Ala Gly Arg Asn Cys Ser Phe Gln
            835                 840                 845

Pro Glu Arg Tyr Ser Val Ser Thr Arg Ile Val Cys Val Ile Glu Ala
850                 855                 860

Ala Glu Thr Pro Phe Thr Gly Val Glu Val Asp Val Phe Gly Lys
865                 870                 875                 880

Leu Gly Arg Ser Pro Pro Asn Val Gln Phe Thr Phe Gln Gln Pro Lys
                885                 890                 895

Pro Leu Ser Val Glu Pro Gln Gln Gly Pro Gln Ala Gly Gly Thr Thr
            900                 905                 910

Leu Thr Ile His Gly Thr His Leu Asp Thr Gly Ser Gln Glu Asp Val
            915                 920                 925
```

```
Arg Val Thr Leu Asn Gly Val Pro Cys Lys Val Thr Lys Phe Gly Ala
    930                 935                 940

Gln Leu Gln Cys Val Thr Gly Pro Gln Ala Thr Arg Gly Gln Met Leu
945                 950                 955                 960

Leu Glu Val Ser Tyr Gly Gly Ser Pro Val Pro Asn Pro Gly Ile Phe
                965                 970                 975

Phe Thr Tyr Arg Glu Asn Pro Val Leu Arg Ala Phe Glu Pro Leu Arg
            980                 985                 990

Ser Phe Ala Ser Gly Gly Arg Ser Ile Asn Val Thr Gly Gln Gly Phe
        995                1000                1005

Ser Leu Ile Gln Arg Phe Ala Met Val Val Ile Ala Glu Pro Leu
    1010                1015                1020

Gln Ser Trp Gln Pro Pro Arg Glu Ala Glu Ser Leu Gln Pro Met
    1025                1030                1035

Thr Val Val Gly Thr Asp Tyr Val Phe His Asn Asp Thr Lys Val
    1040                1045                1050

Val Phe Leu Ser Pro Ala Val Pro Glu Glu Pro Glu Ala Tyr Asn
    1055                1060                1065

Leu Thr Val Leu Ile Glu Met Asp Gly His Arg Ala Leu Leu Arg
    1070                1075                1080

Thr Glu Ala Gly Ala Phe Glu Tyr Val Pro Asp Pro Thr Phe Glu
    1085                1090                1095

Asn Phe Thr Gly Gly Val Lys Lys Gln Val Asn Lys Leu Ile His
    1100                1105                1110

Ala Arg Gly Thr Asn Leu Asn Lys Ala Met Thr Leu Gln Glu Ala
    1115                1120                1125

Glu Ala Phe Val Gly Ala Glu Arg Cys Thr Met Lys Thr Leu Thr
    1130                1135                1140

Glu Thr Asp Leu Tyr Cys Glu Pro Pro Glu Val Gln Pro Pro Pro
    1145                1150                1155

Lys Arg Arg Gln Lys Arg Asp Thr Thr His Asn Leu Pro Glu Phe
    1160                1165                1170

Ile Val Lys Phe Gly Ser Arg Glu Trp Val Leu Gly Arg Val Glu
    1175                1180                1185

Tyr Asp Thr Arg Val Ser Asp Val Pro Leu Ser Leu Ile Leu Pro
    1190                1195                1200

Leu Val Ile Val Pro Met Val Val Ile Ala Val Ser Val Tyr
    1205                1210                1215

Cys Tyr Trp Arg Lys Ser Gln Gln Ala Glu Arg Glu Tyr Glu Lys
    1220                1225                1230

Ile Lys Ser Gln Leu Glu Gly Leu Glu Glu Ser Val Arg Asp Arg
    1235                1240                1245

Cys Lys Lys Glu Phe Thr Asp Leu Met Ile Glu Met Glu Asp Gln
    1250                1255                1260

Thr Asn Asp Val His Glu Ala Gly Ile Pro Val Leu Asp Tyr Lys
    1265                1270                1275

Thr Tyr Thr Asp Arg Val Phe Phe Leu Pro Ser Lys Asp Gly Asp
    1280                1285                1290

Lys Asp Val Met Ile Thr Gly Lys Leu Asp Ile Pro Glu Pro Arg
    1295                1300                1305

Arg Pro Val Val Glu Gln Ala Leu Tyr Gln Phe Ser Asn Leu Leu
    1310                1315                1320
```

```
Asn Ser Lys Ser Phe Leu Ile Asn Phe Ile His Thr Leu Glu Asn
    1325                1330                1335
Gln Arg Glu Phe Ser Ala Arg Ala Lys Val Tyr Phe Ala Ser Leu
    1340                1345                1350
Leu Thr Val Ala Leu His Gly Lys Leu Glu Tyr Tyr Thr Asp Ile
    1355                1360                1365
Met His Thr Leu Phe Leu Glu Leu Leu Glu Gln Tyr Val Val Ala
    1370                1375                1380
Lys Asn Pro Lys Leu Met Leu Arg Arg Ser Glu Thr Val Val Glu
    1385                1390                1395
Arg Met Leu Ser Asn Trp Met Ser Ile Cys Leu Tyr Gln Tyr Leu
    1400                1405                1410
Lys Asp Ser Ala Gly Glu Pro Leu Tyr Lys Leu Phe Lys Ala Ile
    1415                1420                1425
Lys His Gln Val Glu Lys Gly Pro Val Asp Ala Val Gln Lys Lys
    1430                1435                1440
Ala Lys Tyr Thr Leu Asn Asp Thr Gly Leu Leu Gly Asp Asp Val
    1445                1450                1455
Glu Tyr Ala Pro Leu Thr Val Ser Val Ile Val Gln Asp Glu Gly
    1460                1465                1470
Val Asp Ala Ile Pro Val Lys Val Leu Asn Cys Asp Thr Ile Ser
    1475                1480                1485
Gln Val Lys Glu Lys Ile Ile Asp Gln Val Tyr Arg Gly Gln Pro
    1490                1495                1500
Cys Ser Cys Trp Pro Arg Pro Asp Ser Val Val Leu Glu Trp Arg
    1505                1510                1515
Pro Gly Ser Thr Ala Gln Ile Leu Ser Asp Leu Asp Leu Thr Ser
    1520                1525                1530
Gln Arg Glu Gly Arg Trp Lys Arg Val Asn Thr Leu Met His Tyr
    1535                1540                1545
Asn Val Arg Asp Gly Ala Thr Leu Ile Leu Ser Lys Val Gly Val
    1550                1555                1560
Ser Gln Gln Pro Glu Asp Ser Gln Gln Asp Leu Pro Gly Glu Arg
    1565                1570                1575
His Ala Leu Leu Glu Glu Glu Asn Arg Val Trp His Leu Val Arg
    1580                1585                1590
Pro Thr Asp Glu Val Asp Glu Gly Lys Ser Lys Arg Gly Ser Val
    1595                1600                1605
Lys Glu Lys Glu Arg Thr Lys Ala Ile Thr Glu Ile Tyr Leu Thr
    1610                1615                1620
Arg Leu Leu Ser Val Lys Gly Thr Leu Gln Gln Phe Val Asp Asn
    1625                1630                1635
Phe Phe Gln Ser Val Leu Ala Pro Gly His Ala Val Pro Pro Ala
    1640                1645                1650
Val Lys Tyr Phe Phe Asp Phe Leu Asp Glu Gln Ala Glu Lys His
    1655                1660                1665
Asn Ile Gln Asp Glu Asp Thr Ile His Ile Trp Lys Thr Asn Ser
    1670                1675                1680
Leu Pro Leu Arg Phe Trp Val Asn Ile Leu Lys Asn Pro His Phe
    1685                1690                1695
Ile Phe Asp Val His Val His Glu Val Val Asp Ala Ser Leu Ser
    1700                1705                1710
Val Ile Ala Gln Thr Phe Met Asp Ala Cys Thr Arg Thr Glu His
```

```
                 1715                1720                1725

Lys Leu Ser Arg Asp Ser Pro Ser Asn Lys Leu Leu Tyr Ala Lys
        1730                1735                1740

Glu Ile Ser Thr Tyr Lys Lys Met Val Glu Asp Tyr Tyr Lys Gly
    1745                1750                1755

Ile Arg Gln Met Val Gln Val Ser Asp Gln Asp Met Asn Thr His
1760                1765                1770

Leu Ala Glu Ile Ser Arg Ala His Thr Asp Ser Leu Asn Thr Leu
    1775                1780                1785

Val Ala Leu His Gln Leu Tyr Gln Tyr Thr Gln Lys Tyr Tyr Asp
    1790                1795                1800

Glu Ile Ile Asn Ala Leu Glu Glu Asp Pro Ala Ala Gln Lys Met
        1805                1810                1815

Gln Leu Ala Phe Arg Leu Gln Gln Ile Ala Ala Ala Leu Glu Asn
    1820                1825                1830

Lys Val Thr Asp Leu
    1835

<210> SEQ ID NO 5
<211> LENGTH: 147
<212> TYPE: PRT
<213> ORGANISM: Homo sapiens

<400> SEQUENCE: 5

Met Val Met Gly Leu Gly Val Leu Leu Leu Val Phe Val Leu Gly
1               5                   10                  15

Gly Leu Thr Pro Pro Thr Leu Ala Gln Asp Asn Ser Arg Tyr Thr His
            20                  25                  30

Phe Leu Thr Gln His Tyr Asp Ala Lys Pro Gln Gly Arg Asp Asp Arg
        35                  40                  45

Tyr Cys Glu Ser Ile Met Arg Arg Gly Leu Thr Ser Pro Cys Lys
50                  55                  60

Asp Ile Asn Thr Phe Ile His Gly Asn Lys Arg Ser Ile Lys Ala Ile
65                  70                  75                  80

Cys Glu Asn Lys Asn Gly Asn Pro His Arg Glu Asn Leu Arg Ile Ser
                85                  90                  95

Lys Ser Ser Phe Gln Val Thr Thr Cys Lys Leu His Gly Gly Ser Pro
            100                 105                 110

Trp Pro Pro Cys Gln Tyr Arg Ala Thr Ala Gly Phe Arg Asn Val Val
        115                 120                 125

Val Ala Cys Glu Asn Gly Leu Pro Val His Leu Asp Gln Ser Ile Phe
    130                 135                 140

Arg Arg Pro
145

<210> SEQ ID NO 6
<211> LENGTH: 25
<212> TYPE: PRT
<213> ORGANISM: Homo sapiens

<400> SEQUENCE: 6

Ser Phe Val Ala Ser Asn Asp Glu Gly Val Ala Thr Val Gly Leu Val
1               5                   10                  15

Ser Ser Thr Gly Pro Gly Gly Asp Arg
            20                  25
```

-continued

```
<210> SEQ ID NO 7
<211> LENGTH: 18
<212> TYPE: PRT
<213> ORGANISM: Homo sapiens

<400> SEQUENCE: 7

Val Asp Val Ser Gln Gln Pro Glu Asp Ser Gln Gln Asp Leu Pro Gly
1               5                   10                  15

Glu Arg

<210> SEQ ID NO 8
<211> LENGTH: 16
<212> TYPE: PRT
<213> ORGANISM: Homo sapiens

<400> SEQUENCE: 8

Leu Gln Leu Glu Gln Gln Val Ala Thr Gly Pro Ala Leu Asp Asn Lys
1               5                   10                  15

<210> SEQ ID NO 9
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Oxidized Met

<400> SEQUENCE: 9

Ala Met Thr Leu Gln Glu Ala Glu Ala Phe Val Gly Ala Glu Arg
1               5                   10                  15

<210> SEQ ID NO 10
<211> LENGTH: 16
<212> TYPE: PRT
<213> ORGANISM: Homo sapiens

<400> SEQUENCE: 10

Leu Pro Val Gln Glu Cys Leu Ser Tyr Pro Thr Cys Thr Gln Cys Arg
1               5                   10                  15

<210> SEQ ID NO 11
<211> LENGTH: 15
<212> TYPE: PRT
<213> ORGANISM: Homo sapiens

<400> SEQUENCE: 11

Asp Ser Gln Asp Pro Tyr Cys Gly Trp Cys Val Val Glu Gly Arg
1               5                   10                  15

<210> SEQ ID NO 12
<211> LENGTH: 15
<212> TYPE: PRT
<213> ORGANISM: Homo sapiens

<400> SEQUENCE: 12

Ala Met Thr Leu Gln Glu Ala Glu Ala Phe Val Gly Ala Glu Arg
1               5                   10                  15

<210> SEQ ID NO 13
<211> LENGTH: 13
<212> TYPE: PRT
<213> ORGANISM: Homo sapiens

<400> SEQUENCE: 13
```

Ser Pro Pro Asn Val Gln Phe Thr Phe Gln Gln Pro Lys
1               5                   10

<210> SEQ ID NO 14
<211> LENGTH: 13
<212> TYPE: PRT
<213> ORGANISM: Homo sapiens

<400> SEQUENCE: 14

Glu Ala Phe Glu Ala Tyr Thr Asp His Ala Thr Tyr Lys
1               5                   10

<210> SEQ ID NO 15
<211> LENGTH: 12
<212> TYPE: PRT
<213> ORGANISM: Homo sapiens

<400> SEQUENCE: 15

Glu Ala Ser Pro Asn Pro Glu Asp Gly Ile Val Arg
1               5                   10

<210> SEQ ID NO 16
<211> LENGTH: 11
<212> TYPE: PRT
<213> ORGANISM: Homo sapiens

<400> SEQUENCE: 16

Leu Gln Gln Ile Ala Ala Ala Leu Glu Asn Lys
1               5                   10

<210> SEQ ID NO 17
<211> LENGTH: 10
<212> TYPE: PRT
<213> ORGANISM: Homo sapiens

<400> SEQUENCE: 17

Leu Phe Tyr Glu Asp Gly Ser Gly Glu Lys
1               5                   10

<210> SEQ ID NO 18
<211> LENGTH: 9
<212> TYPE: PRT
<213> ORGANISM: Homo sapiens

<400> SEQUENCE: 18

Ala Ile Thr Glu Ile Tyr Leu Thr Arg
1               5

<210> SEQ ID NO 19
<211> LENGTH: 9
<212> TYPE: PRT
<213> ORGANISM: Homo sapiens

<400> SEQUENCE: 19

Asp Gly Ala Thr Leu Ile Leu Ser Lys
1               5

<210> SEQ ID NO 20
<211> LENGTH: 9
<212> TYPE: PRT
<213> ORGANISM: Homo sapiens

<400> SEQUENCE: 20

Cys Ala Trp Cys Gly Gly Gln Ser Arg
1               5

```
<210> SEQ ID NO 21
<211> LENGTH: 8
<212> TYPE: PRT
<213> ORGANISM: Homo sapiens

<400> SEQUENCE: 21

Val Leu Tyr Ala Val Phe Ser Arg
1               5
```